(12) United States Patent
Shen et al.

(10) Patent No.: US 9,771,596 B2
(45) Date of Patent: Sep. 26, 2017

(54) USE OF AUXIN SYNTHASE FOR IMPROVING CROP YIELD

(71) Applicant: Hangzhou Ruifeng Biotechnology Limited Inc., Hangzhou (CN)

(72) Inventors: Zhicheng Shen, Hangzhou (CN); Xianwen Zhang, Hangzhou (CN)

(73) Assignee: HANGZHOU RUIFENG BIOTECHNOLOGY LIMITED INC., Hangzhou, Zhejiang Province (CN)

( * ) Notice: Subject to any disclaimer, the term of this patent is extended or adjusted under 35 U.S.C. 154(b) by 55 days.

(21) Appl. No.: 14/369,334

(22) PCT Filed: Dec. 26, 2012

(86) PCT No.: PCT/CN2012/087542
§ 371 (c)(1),
(2) Date: Jun. 27, 2014

(87) PCT Pub. No.: WO2013/097722
PCT Pub. Date: Jul. 4, 2013

(65) Prior Publication Data
US 2015/0184183 A1    Jul. 2, 2015

(30) Foreign Application Priority Data

Dec. 29, 2011   (CN) .......................... 2011 1 0450964

(51) Int. Cl.
*C12N 15/82* (2006.01)
*C12N 9/88* (2006.01)

(52) U.S. Cl.
CPC ........... *C12N 15/8229* (2013.01); *C12N 9/88* (2013.01); *C12N 15/8261* (2013.01)

(58) Field of Classification Search
None
See application file for complete search history.

(56) References Cited

U.S. PATENT DOCUMENTS 6,455,760 B1 * 9/2002 Zhao .................... C12N 9/0071
                                                435/410
2011/0145947 A1    6/2011 Pei et al.

FOREIGN PATENT DOCUMENTS

| CN | 102137933 A | 7/2011 |
|---|---|---|
| CN | 102 296 085 A | 12/2011 |
| WO | WO 2004/000015 A2 | 12/2003 |
| WO | WO 2008/005988 A2 | 1/2008 |
| WO | WO 2010/124953 A1 | 12/2010 |

OTHER PUBLICATIONS

Kaur et al, The Plant Cell, Mar. 2006, col. 18, pp. 545-559.*
Extended European Search Report for corresponding European Application No. 12863051.4, mailed Jul. 22, 2015.
Csukasi, F., et al., "Modification of Plant Hormone Levels and Signaling as a Tool in Plant Biotechnology," *Biotechnology Journal*, 2009, pp. 1293-1304, vol. 4.
Lee, J.-H., et al., "Conservation and Divergence of FCA Function Between *Arabidopsis* and Rice," *Plant Molecular Biology*, 2005, pp. 823-838, vol. 58.
MacKnight, R., et al., "Functional Significance of the Alternative Transcript Processing of the Arabidopsis Floral Promoter *FCA*," *The Plant Cell*, Apr. 2002, pp. 877-888, vol. 14.
Mezzetti, B., et al., "The defH9-iaaM auxin-synthesizing gene increases plant fecundity and fruit production in strawberry and raspberry," *BMC Biotechnology*, Mar. 15, 2004, vol. 4(4).
Tabata, S., et al., "Evidence of meiosis-specific regulation of gene expression in lily microsporocytes," *Plant Science*, 1993, pp. 31-41, vol. 89.
Wang, L., et al., "Functional analysis of an iaaM gene in parthenocarpic fruit development in transgenic *Physalis pubescens* L. plants," *Plant Cell, Tissue and Organ Culture*, 2011, pp. 333-340, vol. 107.
Genbank Accession No. P06617, "Full-Tryptophan 2-monooxygenase," 1991, pp. 1-7.
Zhao, Z., et al., "Construction of Seed-specific Expression Vector of Auxin Synthesis Gene iaaM and Regeneration of Transgenic Brassica napus L," *Journal of Henan Agricultural Sciences*, 2008, No. 9, pp. 39-44.

* cited by examiner

*Primary Examiner* — Eileen O Hara
(74) *Attorney, Agent, or Firm* — Womble Carlyle Sandridge & Rice LLP

(57) ABSTRACT

Compositions and methods for increasing plant yield are provided. The methods comprise increasing the expression of an anxin synthase gene or coding sequence in the shoot meristem and inflorescence of a plant. The compositions comprise DNA constructs comprising an auxin synthase coding sequence operably linked to a promoter that preferentially drives expression in the shoot meristem and inflorescence of a plant. Also provided are plants, plant cells, plant tissues, and seeds that have been transformed with the DNA construct.

15 Claims, No Drawings

SEQUENCE LISTING

<160> NUMBER OF SEQ ID NOS: 35

<210> SEQ ID NO 1
<211> LENGTH: 1839
<212> TYPE: DNA
<213> ORGANISM: Oryza sativa

<400> SEQUENCE: 1

```
aagcttgaaa ctagtactag acattactct tccaatgcaa acaccactat tccatactta       60
aatttaatgc tatttatatc acatgatgtc ttggatgttg tgtagaaact atatctcatg      120
caagacatga tttccttctc tttcctcatt tatttacttg ccacatcatt tttcatccta      180
ggtgacaact tatttaatgc tatggacact atcctagtca ttgggttggg aatggcctta      240
ctccctccat tccaaaatag cacaactact cttaacccaa aaaacaaaaa ataattatta      300
tcatattata gtttgaatga tcctaataaa tataatgcat atatccaata tgattagata      360
acatgagagt gaaggattta aaaataataa taatttaatg gagaagatgc catagttaat      420
tgtatacttg catgcatgcc ttatattatg gaacatctaa gaaaattggt tgtgctttat      480
attatgcaat ggagggagtg tcttaaaaaa tatactccag tttgtaattc taacatatta      540
ccatgttaat tggataaaaa ttatatatgt tagatggtgg tggattgaaa ttataatggt      600
tgatataatt atattcgaaa cacaaatagc atatgtggag attgaagcta taagatgtat      660
ttcaaataga atcctactta aatctactgt atgcaaatgt atctttggaa aaagctacga      720
attacattaa gaaaatgtat tttctaatat acactttctc tatcgtaaaa tatagctatc      780
tatagcattt aaaaattatc ataaaatata acaacttcta taccaatcac aaccttcgac      840
attcaaattc tccacctagt ccttcttaac caaacatttc ttttctcatt taattttatc      900 tacttttttta atcccttata tccaaactta aaactttcta tttagaatgg aggtaattct      960
gtatatagat taccaaaagg tacaagagct aagaatcgtg catcaaattc acttcggaaa     1020
attacataag aaaaacattt gctagtttgt tctacataaa tctcgagaat tttcacaacg     1080
gaacacgaag ctaggagaat ttcacattt ataaacttt tataaaatga ttaaaaaata      1140
ttgaaaaata aattaaaaaa atctaaagtc aacttcaaat taaaaaatta aaattaaaat     1200
tttggctaat aaacatagca aaagccgaaa gatgagacta aaagctaccc agatcaaaca     1260
gttctatcgc tatagaagat ccgagcaaaa aacagggccg gccggccggc agaagaacac     1320
accacaccac tccccagtcc ccagcccacc cccacccccc ccctcgtgg cactgtagcc      1380 agtgtactat actgccctgc ccttcaccac tttcacctcc ctcctcgagt cttctcctct     1440
```

```
cgtctccccc tctccctctc ctctccgcca ccacgccacc gtgcttccct cccctttgtt    1500
cctgtagcgt tccgaataaa agcccacctg ctttcctttc ccgcgaccat taccataaaa    1560
agagcttgct cccaccgcct ctctctctat ctccccgtcg ctagctacca gcagcaacaa    1620
gtacactccc cccactcctc ccccacacgc cgcgtacaac tagctaagca gaggagaggg    1680
agagagagag aggtggggtt ttgatggaag tacaattcta gctatgttct tgatcggggc    1740
catgatcgcg gatctctaga aagttctaga tcttccgtgc gtggtgggcg ggtggggtg    1800 ttcttggtag ggtaggtaag tgctgctgca ggatcctct                            1839

<210> SEQ ID NO 2
<211> LENGTH: 1421
<212> TYPE: DNA
<213> ORGANISM: Zea mays

<400> SEQUENCE: 2
agaaagctta gtgccaatca ctgcgtgaga accgacggcg gtgctcactg cacaggcgcg      60
gacggtccgc ggtcaggggc cgaacgatcc gcgacctggc gcaggGCTTA ggatttcctg     120
cctgacggtc ggacagtccg cgtctacagg ccggacggtc cgcgcgtgcg caggggcggc     180
gaaggtcgcc ggcgacgcct ggatctcgcc ccgagaggga cccgtcggg gaggagagat     240 cttaggtgtt gtctaggctt ggtaggccga cctagacttc tctaatcgac gtagagtcga     300
agagaagcag agaatttggg gattggaagg ctaaactcga actagactag aactaaatac     360
gagataaact ggtattgatt cgattgatga tgtttaatcg gctgtattcc tctgtattta     420
tagaggaggg ggctggaccc gttagagaca gattttccga gctaattccg tgaatcttgc     480
caacaactat agcaagaaac tcggaactct aactggttct acgtgcgcgc ggaccgtccg     540
gaccagcgat gcgggccgtc tggccctcta tttggtgctc accggaacca tgtcttacca     600
atgtgttgaa attgttttat ggcgaacata aaatctaaa gttgtaattt ttaaaataaa      660
gccctcctaa acagaacatt aattttata attgatattc aaatatttta gtccggtaac      720
caaacgccca gtaatttgaa gaatatggtc tttatttgta gccggcggca tctcgaaaag    780
ctagatctaa ctccgaaaac aaacacgcaa aatctaccgg aaaaatctcc cccagcaaag    840
aagcagacgt ggggcctgtc atgtacgcac ggggcatgac tcgtgcaaga gcaacaagtg    900
ctgtcgttgc agaggatccg agctaaaaca atccagcaca cggccactct cgtctctcct    960
cttcctcctc ttccctccgt accgcccgcc cttcacctcc tcgactcttc tccaccgccc   1020
cctccctcct cgcgtctctc tccccctttg tccctgtaga gctccaaata aaaccccacc   1080
ggttttcttt tcccgcggca attaccataa aaagagctcc caatctctct tcctctctc    1140 cggcccctct ctctcgtttc tggcaggagt ggtgcggtac taccaccgct ctctcactcc   1200
acacacacac accgagtata cggctaagca ggagagagaa cgggagagtg agactgagac   1260
ggggtcccaa gtacaattct cgcctggttc ttgatcgaag gcatgatcaa gaatcaccag   1320
aaagttctag atctttagac ggcagtcttc cttggactcc tcggtttctt ttgttctgag   1380
ctctagccat ggagggtggg ggagggagtg gaggatcccc t                        1421

<210> SEQ ID NO 3
<211> LENGTH: 2578
<212> TYPE: DNA
<213> ORGANISM: Glycine max

<400> SEQUENCE: 3
aggaagcttg aaagaacgta gtcccttctt aaaaatggtg aagaggcagg gaaacatcgc      60
```

```
tttcacttac ttttagtgcc acatcaaacg ggttttgttt gtttagtggc aactgccaaa    120
caagagatag agtcattcat agagggctag agattagaga agtcacggtt ggctgctggc    180
ctgttcaaat ggtacgaata atgtggaaca atttaaacaa catgttacat tttttttctat   240 attttcctat aaatctttt aatagttcat acaaaatata ataaaaaat ataaataaaa       300 aataaatatg ttcaatatct tagatacata aaaaaaatgc ctaatagtac tttttatcta    360
acaagttaga taattaataa gaattttta tagaaaaatt aaaagtaaa tgggattaat      420 gaactaatat ttttttttaa taactaaaat caaatttaac tatattgtca gaaactaaaa    480
atatattttg ctcataaatt tatataactg ataatttact tacttattac ttaattctat    540
atttaatcat aaacattaaa gttacaaaca tcttaattaa ttgtaggtaa tttattagtt    600
aaatgagatt aatatatta gttaatatgg aaaaggttgt gtaaaattaa catgtattag     660
gaaaagtgtg tgagaaatta gtgaaagaaa caaaaaatac ttgcatggag attagaaaag   720
gatgggacaa tgagagacgt ggaagatgga ggcagtgtca ttcatgcaaa gaatcaaatg   780
cttagaataa aatagcattg gtgtggtgtt gaggctagga gagcttcaaa acttgagaaa   840
tctcaccttt cactgcagat tggaatccta actcaactca atgagacaat tattaaactt   900
attgtaaggc tatcaccaac cccccgtcat ctctcccagt atctttaacc acagtgacaa   960
tgggaactga aattcgtttt tctttattaa taatccaacc actatttgca gaagagccat  1020
ccggagttgt ctgcacataa caagacaaat aatataccaa tacaaattat tgggaaaaac  1080
ttaattacta ccaataatca aacgcaaggc aacttgtggc tatgttttgg gcctaaatta  1140
aattaataat gagatgagaa aggagagcag tgaaaatagc tagataagaa aaactgtcac  1200
aaaattctgt gtgtgtaagg aagtgttcac agatgaagca ttatgagcag tagaaaaata  1260
caaaaacatg aaatagtacg gtacccaggc tgccaagcag gcaccggagc catttattgt  1320
tgtcctcttt tggcatttgt tgtttttata cagaattgca aattcaacgt tgaatgaaaa  1380
ttgcctaaat agttggatta atcatcatgg ttttaaaatg tgaatgaaaa ggtgttacag  1440
gaaattatat ttgcagactc aaatggaaga tatgaccta gtcaaacagt ccatttactg   1500
ggttctgatt tgactattgg acttgttaaa gaaatagact tgatattctt ttaaatacta  1560
ggatgatatt tgaaaaaaat aatactagct ataactcaaa acatattgaa tacacctcat  1620
tggatgtttg tttagaatag tctaaattat aacaaataat tatttgtatt ttaagtctct  1680
ttcaaaaagc taacaagaat atgaactctt tttccctca aaataaagct catgccaaat   1740
aacttaactt tttcttaaaa ataataataa atattgttta tgttttgaat atgaagaatg  1800
ctttaatatc tgacaatttt ttttattaaa attaattaat actagattaa gtggtgacat  1860
aaattaaaac tattttttt agatgagtga taggaacaca ctttataata tagtcttttt   1920
aatatatttt tttattgatt aatttattaa aactataaaa tcaagaaaaa taattattaa  1980
ataaaatatg agacgtattg aattttatga tttcctataa atttaagtta tgatattcat  2040
atacatcatt tttggatgaa ataaaagaga gagagaaaga aaaaaaagaa tagaaagaga  2100
aaataataaa tgtgataaat gatatgataa aaaggaaaga gaaagataga gaaataattg  2160
gaggaaaggt ggaatgaaag agaaaataaa atattttgt atttatctaa ctaatatgtt   2220
tatatttagc caattgtttg aagacattag ttaaagaacc taaaataaaa ataatttatt  2280
ggaaaaaaat tgaattattc ataatctatc ttatattttc ttataattta gataataaat  2340
atatttagat aagtatttgt agcatataaa taaagaatga aaatgacaat gaagcaaaac  2400
```

-continued

| | | |
|---|---|---|
| caccaaaatg gtgagtcctt agtcagtagc tgtggtgtgc aaagggagaa aagagagggg | 2460 | |
| taataaagta aaaggggatg ggggcattag gtgggaaagt acttttgag taagttttg | 2520 | |
| ggttaggaaa gtagagaatg aggaaaagag gcgagtgagt gagatttgag gatcccct | 2578 | |

<210> SEQ ID NO 4
<211> LENGTH: 2973
<212> TYPE: DNA
<213> ORGANISM: Glycine max

<400> SEQUENCE: 4

| | |
|---|---|
| aagcttttaa actaatttta tcttatttaa tattattatc tcttaaatac tattcattta | 60 |
| attgaggtat tagttttaat atctctttct aatccttgaa atcaaattcc aattaataat | 120 |
| aaattgaaaa atatatattt tcaattaaag ttaatacaat taaatatcca ctttgcacat | 180 |
| gtttcattaa atattcactt tcaattaatt cttcattaac taattaatta tgattctttg | 240 |
| gaaggaaaaa aaaacaaat ttctctctct tatttatttt ataaaatcac cttaatgtat | 300 |
| tctctctctt cccactaaaa taataattaa tattgtacat tcataaaata aataaataac | 360 |
| gaaaattgtt ttttaaaaat aattaatgat gttgttgatg taaggaaatg tattttttaat | 420 |
| gccctcctac ggttctaccg ggaaatgcaa atctcaaggga taaagcaggg tgctcaatag | 480 |
| ccgtgaaaat tttcaacgtt gatgaaactg tattttttga caagacgaca ataaagcaac | 540 |
| aaacaagaaa gaaagaggtc gattgatgaa ttgccaaaca aatccgaacg tcaatgtgct | 600 |
| ttgttagaaa cgtagtccct tcttaaaatt gctcaagagg cagggaaaca tcgctttcac | 660 |
| tcacttttgg tgcccacatca aacgggtttt ctttgtttaa tgccaacggc caaacaaaca | 720 |
| agaaatagag aggggcagag aagtcatgct tggctactct cctgtgcaaa tgctacaatt | 780 |
| taagcaacac taatgttaca ttttagttt ttatctaaca agttagataa ttaataagaa | 840 |
| attttgtata aaatttaaa aagtaaatgg gaaaaatgta aagtaatta gggtgatcac | 900 |
| aagtttaact aatatttatt tttttaataa ataactaaaa tcaaatttag ctatattgac | 960 |
| aaaaactgaa aacatatttt aatttcctca tatatttata caattgatga tttacttgat | 1020 |
| tgttactttg ttatatattt aattataaat attaacgtta cataactctt aattagttaa | 1080 |
| aggtaattta ttgattaaat gagattaata tatttagtta atatggaaaa gttgtgtaaa | 1140 |
| acatgtatta ggaaaagtat gagaaattag tgaaggaaca aaaaaaatac ttgcatggag | 1200 |
| actaggaaag gacaatgaga gacgtggaag atggaggcag tgccattcat gcaaataatt | 1260 |
| aattaaatac tcggaataaa atagcttggg tgtggtgttg aggctaattg gaatcctaac | 1320 |
| tcaactcaat gggaactgaa attcgttttt cttcattaat catccaacca ctatttacat | 1380 |
| aagagccatc cagagttgtc tgcatataac aagacccttt tgagtgcctt ttttggattt | 1440 |
| taattaagat gcatattatt ttaaattttt cactttatat gccttgacga ctaatatacc | 1500 |
| aatacaaatt attatgggcc taaatgaaat gaatatgatg agaaaaggga gcagtgaaaa | 1560 |
| tagctaagaa aaactgaatc acaaaattca gtgtgtaagg aagtgttcac agataaagca | 1620 |
| ctatgagcag tagaaaatac aaaaacatga atagtacgg tacccaagct gccaagcagg | 1680 |
| catcggagcc atttattgct gtcctctttt ggcatctgtt gcttttatac agcattgtaa | 1740 |
| gtgcaacgtt gaatggaaaa taacctaaat aattgattaa tcagcatggt ttttaaatgt | 1800 |
| gaatgaaaag gtgttacagg aaattatatt tgcaaactca aatggaagtc aaacagtcca | 1860 |
| tttattgggt tctgatttga ctatgggact tgttaaaaaa catcacttgt attttttaaat | 1920 |
| taaatactag aatgatataa tcaaaagttg gtataatgat ggaatatttt attgtattca | 1980 |

```
tatgagtgaa aataatatat ttaatgtgtt agtttggaat atattctttt tgtataggtt    2040
aaaatttatt aaaaaaatta taaaataaaa aaaataatta ttaaataaga tgtgaaaatt    2100
tttaaatttt tttatcaata aattttaact agtaaaaaat agtgtatttc aagtattttt    2160
ttttcttttg caaaaccagc aaaaattaat acggttagta agaattgagt tcatatatct    2220
taagaccata aatttgagtc ttaatgtcaa atgtaagaat ttttttaata gataatcttt    2280
caagaaatta ttaaataatc tagaattact aggtgaccat attttcaacc attgtttata    2340
ctactataac acatttgaaa ttaacaatta accaaaataa taataaattt ttagtatatg    2400
tcatatgaaa attaattaag atcataaaaa ttttgatgta tctaattatt tttcgtgagg    2460
agtgttagaa atatatcttc agtaagctcc tccaaacatg cattatctaa ttggttaaaa    2520
tttatgaaaa attatagaat taggaagaaa aaaagttatt aaatataatg caagacacac    2580 taaatttat tattttaat aaatttcaag aaaatataaa aagatgtgta ttcttaaccg    2640
ttctttctca attttcata atatgtaagt agcagtggaa aagttattta ttaagcagtt    2700
tgaaacaata acttggccat agtcactacc aatatttata tttatgagag acatggttca    2760
acttttgaat ttgtgagaac taattaatac tggccagtta tatagtatgc agtagtgtaa    2820
aaatgaatga aaatcataat gatccaaaac agagccagca ctggctaact cagctcatgg    2880
tgtggtgtgg ggaggggtaa taaagtaaaa taggggttgtg gcattaggtg ggaaagtaca    2940
tttttagcaa ctttgggttg gataggagga tcc                                 2973

<210> SEQ ID NO 5
<211> LENGTH: 1786
<212> TYPE: DNA
<213> ORGANISM: Arabidopsis thaliana

<400> SEQUENCE: 5
aggaagctta cttcgtgttt aacaaacact ttccttcact atactagtat ccacattaaa      60
caatgatatt gcttttttaaa gataaatttga ttctaatatc attaaaacct ttttgtatga   120
attttaaact aatgatttcg tgaatgtgtg taataatgta ccctccttgg acagttggac     180
tcgcgataat gtatccttaa gagttaagtc ttttttttc ttctgttttt gggtgcaacc      240
taagagttaa gtctctagct aacttttaac caaaaataga aagtctccag ctaactattg     300
ctagaactta aatgttttgg agattagaca cataaagaaa agaaaacaca cacacacaca     360
ctagatattt tgatattgga gatgctaaaa aatatactca cctcctcaac atatgacaaa     420
atgaacgaaa aggagggaaa aaaaacacaa agcaaaaaag ctcaattgcg actaaataca     480
aagtgtatga gtactaagcc gcagacaaac cctaagctac attttgtggt gaactatacg     540
tctatacgtc tatacgtcta aaccgaaagc ccaaaggttt atgtggattt aattttgatc     600
tttatttcat aaggttttgt tttgttttcc ttctatgatg tgagattcct tttcgagtcg     660
aacttacctc tttaaattac ctcaatttaa aaggttttat gcggactata ctaccaatct     720
ttacctatca cataaacttt agatcccaaa ctaaagtttc gcttgcgtag ctccaagacc     780
agctttggtt actattttt tgttatgatg tctgtctata gaattagtag ctggtattca     840
tatggtttgc ttgataattt atagtcgttg tggttaaagt tcaactgatt attggtccac     900
caaataatat tttctacgat aagttgagaa atttatttag acaatgcagc atgtggtgaa    960
aatatagtta agagttttag acggttaaaa attacaaact atttggaaaa ctacaaaaaa   1020
aaaaaaaatg tttcatattc tccattaaaa tttaattta tcgtttaaac gctaaaatgt    1080
```

| | |
|---|---|
| tgtcaatcga aaatatttag aaccgtatcg tcgttaatcg aaaaaaactc tattatgtta | 1140 |
| ccgctatagt atactttaca ttgatacgat acgacgatgt ataacaaaca atgaaaagtg | 1200 |
| agattcggag tacgaatgcc atatataaga tactgcaaat tatgagtgag acaaaagaaa | 1260 |
| atccaacaaa acaatcaaaa agtaaaattc tccgatagtc caaaaaagtc ttcccataat | 1320 |
| aatcctccga tatattacca taaggtccat aaccattttt tccttatcaa tttatttcta | 1380 |
| atcacattca attagtagct tttctttaca ctgttttaaa aaatactaat cgaaacttaa | 1440 |
| agatgaacat tttccacgta ctcagtattc gtgtcgcgta gggactttct atattacgcc | 1500 |
| tcgtaaaacc aaagaaccca aagcctacaa caaaaagtgc gtaggggtat taacgtaact | 1560 |
| taacaagagg atagtaataa taaattcgat ttaacataaa aacagtcatt ttcgagaaac | 1620 |
| ttaaatgctt acaacacaaa aaaataaaca tttgttctct tccactgtct tgtctgtaat | 1680 |
| aagagcaaag acagagagag acgacgttac agtatctctc tctcacacga tcaagagaaa | 1740 |
| cttcatcatt cgtcggaaaa tatcaactct ggtattagga tccct | 1786 |

<210> SEQ ID NO 6
<211> LENGTH: 2479
<212> TYPE: DNA
<213> ORGANISM: Arabidopsis thaliana

<400> SEQUENCE: 6

| | |
|---|---|
| aagcttaata aattcaaaat cagcacacct aaccacagtg aaaaattatc tgtggaatgt | 60 |
| tcttacataa atacgcttgc aagaaaacgt aaacaatcca acatgacta tcattcatca | 120 |
| gtattctgat ggggagatga catcatcgat cttgattatc ttaactactt gtgttgcaag | 180 |
| tacgatctgt tgctgcttca tgatcaacgt ttcaaacatg ttttgttccc tcatgtgtta | 240 |
| gccctacat cgttgcaatc aatcccgtag aatggaatgt tctcctctcc tgaatattca | 300 |
| acaacaaacc caatacttaa cccatctttc acagtaacaa gccaatatat aaagtaaaca | 360 |
| aagacaaaac acatcaatca cttaccttaa tttgctgaga ttttacagct gagagtgttt | 420 |
| caatgggctg caatccactg ttcaaagcaa gagccatagg gatagaccta agagagatga | 480 |
| gattcaaaag gaagaaacta acatatggtg acatctccgt caggtccttg aagcattttt | 540 |
| tttccatgcc cttgggaccg agagaggatc ggagaatccg agccactgct ttaccagcgg | 600 |
| aaatgttggc ttttgagca tcgatgccct taagacgagt cttttgatct tgctctctta | 660 |
| gtataatgaa cggccggcca aactcatcga aagccaaagc catctctgat tcttcactct | 720 |
| cggcggttcg atccgataca gatctcggat ggtaaaaggt gagagctcaa agaagaagag | 780 |
| tgttaagatt tgagattcaa aacggtcgag acatggtact gagtaaaacc ctaaatcgtt | 840 |
| agaaatggca gattcgtaaa tcaaattgtt tgaagaaaga gctaagaata atatgcacta | 900 |
| cgtgggcctt tggcttatgg cccaatatgc ctatttttct tttactctca ttagcccaac | 960 |
| cggtctcgtg gtaaggtcaa gtaaccatgg gatcgaacaa ataaaagttt gatatttcgt | 1020 |
| ttcaatcact aattggctca ttgcatacca accattctca attttatttt ttaaaagtgg | 1080 |
| aaaatcatat aaacattcat tttaaatttt gaataaataa cacataaaaa atcactaaaa | 1140 |
| taatttacta accaaaagtt gataaaattt ttgaagtata acttcatgtc ttcatcatta | 1200 |
| tgatcacatc atgatgaatc aacaaagttt cttcataatt tattcttaac ttttgtagct | 1260 |
| gaattctgaa ataatatata gaagatattc acgttttcac acttttttta ttattagcta | 1320 |
| gagaatgtag tttatgtaat aaatgaagga tatggtataa acatgacaaa acaaatgac | 1380 |
| agcccaaaac aaggaagtag gtaacaataa cattccttaa aacaaggaat tgccctggtc | 1440 |

-continued

```
cctatttggt cctaccctcg aactataact atatttacat gacatgcgtt tattatatgt    1500
acatagacag atattacgta tgtcaaactc catagctcca aaccattacg tatctgacct    1560
agagggcctc cctaatcctt cttttgtgat aggagattgt agaaaactta taaaaatcta    1620
tgaaacaaaa ggctagatta ggctaatatg ggctaaatgt aatgtaatgt ctatgtgggt    1680
gagatttatt cgttgttttt acgtcaaaag gaatgttgtc actatacatt tatggaacat    1740
aaacaatact acagattatt tagaaatgta taggcttaga tagtttacac tttgcattga    1800
gatggagaga gacacgacaa atcggcccat gcactttgc ggtgaaattg gggaacacga     1860
cattacgaac tattgcaccc aaatacaaat tctatatagt atgatacatg gataatggta    1920
cccaactaat cgaaaattgt gttcctaggc ataaaatcta actatgatat ttgttttaaa    1980
caagaaaaat tctttcgtaa ataatgtttt agagaaaaac atgatttgat tatcttaaaa    2040
actaaatcaa catagaaaaa tgaatgagac tttgttatgt aacctatgtt cttctcgtga    2100
ttattaacaa aaaaacctct acaattgttt gaatactctg cattttccat cagtccattg    2160
caatgaaacc ctctcaaagg acaaaatggt aaattgctcg aacgagttag tacaccatta    2220
aattaaagaa ccttgacttg ttttgttagt aaacaaaaat tgggaaataa aatagaaat     2280 ctctgcagaa taaaaacaaa accaacaaaa attccacttt tgtgctctct ccctctccct    2340 cccttggca ccaaataaag aggtagagag agacgaaata gtacgatcac tgaagaatat     2400
caaacgtcca tagtcattac ctgtcaccgg aaaaaccagt tcccaactca tcacctctcc    2460
ctctaaacca acaggatcc                                                 2479
```

<210> SEQ ID NO 7
<211> LENGTH: 3253
<212> TYPE: DNA
<213> ORGANISM: Arabidopsis thaliana

<400> SEQUENCE: 7

```
agaaagctta cttagcccta tgagcttaac cgaacattct aaattggtgg gttaccgagc     60
attttaatcg gattaaaccg acttgaactg gtatgatgaa aaccttcatt gaaggaattg    120
gacacgttgc ttacgagggg gaaaccaaaa cgttactcca gttaaataat ggcagaagta    180
ttttttgatt gaatgtgatc attatttaaa tgatactact ataaaatgtg taaaagaaac    240
ttgtaatgaa gccaaacaag gccaaacaga atcattacga agtggaagta taaaatgacg    300
taaggtctga ccaaccggtt tctatatatc tcagattttc aaaaatggtt tttgtttcat    360
ccaatactaa aggcagtgta cttaaattca atggaataaa agattgcatt gtccgacgga    420
gatcccaaca caaaacactt gatgaatctt taagctaaac aagtaaacat ttatatactc    480
tatagagtag aatacataaa tagtaagtaa catttaatat ggatcacata aactaattca    540
aagataagaa gctgcagttt tgtaaaata cattcacaga cgagatatcg tacacgacac     600
tcaccttcag ccacatttca cggccgattg gctagctacg tgaatgcatt ccattctat     660 tccttttttt tttttcttc ctattttgc atgttaactt gagacaaaaa gatgaataca     720
tgcattaatg ttggataact attttttttta tagtccaata ccagtctccg atatttatac    780 catctttaa aaacgtttta ttttagatca tcttttgata tttccattaa gtagttcgaa     840
cctagtcatg ctaaatctga taatatggag agatttaacc atcaaacaaa tcaacttcac    900
ttgaagtctt caatagatgc tagctgatta ttattagtat ttagtagttt atttttgtta    960
tggcgccatt cattagattg tactacaaac ttgtaagaat ataaaagtga gacttgactt    1020
```

```
gagaggtagg gaaaacaaca aaacaagaat gataaagaca gtgaatatag aagtaaaagc    1080
aatgattcaa tctcgtcaat aataaaaaaa aactaatgaa tgaaaatagc gtttataaga    1140
tataatcttg aatcaaccaa ccaaacatta tctacaaaga ttattcaatg accagatgaa    1200
gatttatttc tcggtaactt atttagcaac ataagtatct ttttttttt tggaacaaac    1260
ataagatcta tttatatctc aaacaaatgt gaccatatat aattgttata ataagatttc    1320
tttttgggtt taaaaaataa aatcacattt tcaaatttta tttttgcaaa gagtaaagaa    1380
accttaaaac aactagtacc aaacatcttt cttaaactct aactaatata ggattaatgt    1440
tcttttttgca tttaaaatca tgtacgagac taaaacataa gcaaaaatgt gtcaactaaa    1500
aatgtcaact atatcaataa cattaaaaca acctttaat actattttct tccataatac    1560
taagatttga aattctaact ttaatttgtg caagtaaagt tttgtagata aagcaaatga    1620
atcacatgtt taaaagaaa accaaatggt ccattgtttt catagccggc tactttggtt    1680
attagccggg actcgacgac ttgccgtcga gactctcgtg tgagtccgta attatttatt    1740
cttcaactaa aatcaataaa ctattgagtt ataatcataa tcgaatggtc cagattcaag    1800
ctcataccat accactaaat ccatggtaca tacaacgtag cagagtccct ctctccttcc    1860
ttccctcttt tgttttttcc tctccctctc atttttttg ttctctaaac caactaaccg    1920
caaaaaccaa aaaaacccc caaaaaaata aaaatctctc tctcctctcc gtttctctct    1980
ctgtcggagg gagtgccgga atcgcgcgtc gacgggaaga atatcgccgg aaaagctcaa    2040
aaatcatcgc cggtcgcacg aattattcgt tggaaacaac gcgtcgtgag aggaggggaa    2100
attcgaaaag agaagaaaaa aaaattgaaa acgccgattc actttttta tatatataat    2160
ataaaaaatt tcttttacgg aattaaatat tctgtgatgg atgcgattgg atagaaggaa    2220
acaaaaagga aggaggaag ataaaagaga gaagaaggaa ttattctctt ctctcttctc    2280
tttcatctct gtctacatcg ctgtttttt tttttcttcaa ggatcgtgat acctgaagaa    2340
gaagaaggta aaaaataaga gttaacgaga tccactgttt gttgaaaatc tggtttgaat    2400
ttgtttaaga ggaagcataa ttgtgtttgt ttgtgattag gtaagttttc ttattttttt    2460
ggtagctggt ggtgattagg gtttttattt ttatggttta ataatttgga aatggtttaa    2520
ttccgtgccg aatttgtgaa ttaggtaaga gttggttcgc tgtttgatta taatgagctg    2580
cacaaagatc cggtattagg cgaattctac tcttattgct tctggatgta cctaatcgtc    2640
tcttctagat atttctatga gcttaaaatg cagcgatttg atatgttttg cctctctagt    2700
ggttgaagtt gctaactttg ttttatcctt ggacttcgcg taattctagt agaaatcttc    2760
tgtttctcta cttttgtagt tcttttgctt gattttttg gcttgtacgt gagtaattga    2820
gcactttat gtgtcgtttt tgcaagatct tcctcgcaat tgagaaatgc atttttgttta    2880
tgtagacact ggttttgact tgaccacttt tttttttt tttcaggttt tttcagggga    2940
agtgatatgg ttcgttgaaa taagtttaaa gtttaaaag attttgattc tggttttatt    3000
agtcaaattt tgtaagatgc cgtctgatat aatggaacag agaggtgttt caacaccttc    3060
ccactttcat gaagatattc atattacttc agaggtaaac tctttgtttt catttgtttc    3120
aggatttaaa ctgtgtagct ctagaattgc tggtatcata tttctcacgt atgacattat    3180
atctgccact agttttctc aactatactt gtgcttttt gttcggcaga ggcaatttgg    3240
gtttggatcc tct                                                       3253
```

<210> SEQ ID NO 8
<211> LENGTH: 2221

```
<212> TYPE: DNA
<213> ORGANISM: Brassica rupa

<400> SEQUENCE: 8
aagcttccca aatttaatcg aacctaaccg aaaccatttt ggctcgtttg gttttatggc        60
aattctattc aggttagagt ctagttcggt tcgatcatat cttacattta ttttttatttt     120
tattttttt gtactaaata catatattaa atttgataaa aataaattta tattttaagt       180
ttgtgccgta cgtaaaaagg caaatcgtag cttattacaa atagattcaa attatgtata      240
ttaaaaagag aaattccatt agatagtcat tttttagttta ttttcacaaa aataaatttc     300
agggaagaaa atgatcgaaa caagtgttat taaaggataa atatgcaatt atactcaaga     360
gttaattaat ctagacttag ggaaattaaa gttaaggat ggagtttagg gattcaaatt       420
taaaaaaaat aaaaattaaa aattaaaatt ttcaaaacaa aaaggtgcta ttttagtcat     480
tttatttttt gagtgttgtt tttgtgacaa taacttaaaa agtctatttg agagaattgc     540
cttaaaaaaa tcatttactc cttatgttcc taaatgtagg atgtttcaaa aaaaaacatt    600
gatgttcagg aacagaggag tatataccag tgtattattt cttagaaaca taatagtcca    660
cttactaact aaaatgagaa ttaaaaatga tcacatattg taaatttaaa ataacaacag    720
ggttggattt ttttttttt actatagggt tttgtgggtt tggttttgaa tttcagtttg       780
gataaatcaa ttttcgttta ttgtaaaact aaaagtaaac tataaccgag ttttgggtt      840
caaatccgaa ataaatatat acatgtcgat taacaatgat aaagtaagaa gatttagaat    900
tatggaaaga aagaaaacaa tcaaagaata gtgatgccta aaagagattc catagcaatg    960
tcacaaaacg atttttctta tatttttgacc ataacttggt ttgagtcttt gacattgtac   1020
ggttgccaag aagaatcata tttgtacaac aaataagaaa aataaactga agcaaacgtg   1080
gtaagcaaga agttgtatta ctttagtaat ttttttacct ggtaatataa acgaaggaca   1140
agaatcaaga ttatggtttt ggtcgttggt tttgaggagt cttcttctcg aaccgagatt    1200
ttcatgcacg tgtgtttggt cactacttcg tgtttaacaa cactttcttc accataccaa   1260
tatccgcata aaacaaacat ttttctttt ttgaaaaaag gctttctaac ataaaacaaa   1320
aattatttgt taaaacacac aaaatgattg cttttaaatc cttgatcatc tatcattaaa   1380
ccttttttgtt ttattataat aagcaatatg catttaagac tatttgctaa aattatgtaa  1440
caaaggttac gactctagct aactattgcc gttctcaaat gttctacaga ttagaggttg    1500
taaataactt acatactcca tctgtttttt aatgttacat attctagtat tttcacacat   1560
tttaataaaa cacattaaat ttacataatt ttttgtgttt atctttgttc cataatttta   1620
agctaataaa aatttagtac aattaaattt tttgaaattt gtaattagtt aataaaacat     1680
gtcttgaaaa tgtaaaaaat agatttttt taaaacaatt ttttttttaa aatatataat      1740
attaaggaac agagtgagta tatatcaaaa aataaaaaaa tggtccatga tttatttttt   1800
acgtttgttt ttccttcact gcaagttttt ctattcacag tttcaaatat atattttta     1860
aaacagttca caaaggatta acccaggtac tcagtattcc tgcctcgtaa accaagaacc   1920
caagcctaca aaagtgagt aggggtacta aggtaacttc agcaaaatga tagtataatc    1980
catttattta aaaacaacag tcattttcga gaaacataaa tgcgcttata aattggaaag   2040
acataaagaa ataaaacaaa ataaacattt gttctcttcc actgtcttgt ctaatgtctg   2100
tagagtaaag agatagagcc gacgttacag ttatctctct cttctctctc acacgatcaa  2160
gaaaactttc acgttcaccg gtgaaaacta ttactcccgt aagaaaataa ttaaaggatc    2220
```

| c | 2221 |

<210> SEQ ID NO 9
<211> LENGTH: 2212
<212> TYPE: DNA
<213> ORGANISM: Oryza sativa

<400> SEQUENCE: 9

| aagctttgag ggatgttagg tctcgatttt tcaataggta ttgataaaca gtcgaattgg | 60 |
| gcggagtcgc gacacaactc gatccggctt ctgaatgaac acgctattga gccccgcaat | 120 |
| cgcagcacca cgtctcctct ggttatcaac cgtgccgaaa tccggttgac ctcaccaaga | 180 |
| aggctaatcc ctacatgcga atcgaagaac acaagcaaga acaagataga ttgcaaccaa | 240 |
| tttgcatatg aatgattaag cacacgaatt tacaaaccga tctaacggcg aaactgttct | 300 |
| tgacagatta atctaagcaa aacccgactc taaatgatga cggttactga ttaagtatga | 360 |
| ttagggacgt cctagggttg ccctagggcg cacaccccct tgggctaagc ccacgacaca | 420 |
| attacaaggc ccaaaaccca atcagattc ggactggata agatacgtgg cttgttttag | 480 |
| agattcccgg catctcggta ggaattttga cgtgggacca aaccattag agtccataag | 540 |
| cttttccaaca agtactcatg ggccccgaaa ttccttctag atcagcggct aggtccgttt | 600 |
| gaagttgatg ctgtcagaag gcccgaatct gaatccaaaa catgtagaac tttatctctt | 660 |
| atcttctatg gaccaaaagt gacatggtga gatggaagtg gactaggaga aggtcttgat | 720 |
| ttggtcccta atgaacttct ttgatcatcc atgcattcgt tatgctcggt atcttttctt | 780 |
| tcgcccaagc aagtatctct acaaacgaaa acatacaaaa cttattgtgt agcaacgttt | 840 |
| gttcaaatat ataataagta aatctaatgt agaacacatg tacctttggt tgattaatac | 900 |
| ataagatagt catggttata tccgagctag ttgtgtcctc atcatcttgc atgagattta | 960 |
| aaatactcta gagtatgatg atgatatgcc atagtggatg atgatgtgac acagttacat | 1020 |
| gttgagcttt aggagttagt gtgtaccaac tatataaaaa gtagatgtgt gtgaacaaag | 1080 |
| agagtatatg tgtatttata gagatacgtg tatgtacggg tacttaagtc ttgttaacta | 1140 |
| aaaaaaagtc caaacacccc ctatacttta gatgaaagtc tatctagcac cccgaacttt | 1200 |
| aaaactggac atctaatccc ttggtctttg taaaaccgtt catattcccc cctaaggtgg | 1260 |
| ttttgcatat tttggaagct taaacaaaca attttgaata actaatataa catatttgca | 1320 |
| tatcatcaat ttgtacttat atagttatac tatactatta ttatgttggt acttgtttgc | 1380 |
| aaacaagtga gagctaacaa gtgattaaaa agaaagattt aaatggagat tttaatatat | 1440 |
| atgtccaatg tatatgtcac gtgatcaaac tcatccaagt tatatactct ctccgtttca | 1500 |
| agttataaga cgttttgact tcggtcaaag tcaaactgtt tcaagtttga ctaagatcat | 1560 |
| agacaaatat agtaatattt ataatactaa attagtttca ttaaatcaat aattgaatat | 1620 |
| attttcataa taaatttatc ttgggttgaa aatgttacta cttttttcta caaacttggt | 1680 |
| caaacttaaa acaattagac tttgacaaaa atcaaaacgt cttataacct gaaacggaga | 1740 |
| gagtacaaat tagataaaaa ccattataca aaatcacctt aagagataat atgaactgtt | 1800 |
| ttgtaaagtt tagggagtta gatatctagt tttaagtttt aagatgcctt acaaacttct | 1860 |
| atatgtagtt tagagggtat ttggactttt ttttaagaga ataatatatt ttttaatttg | 1920 |
| agcttaaatt ggacgagctc aacgacttct gagttctact acttctgacc aataggcgca | 1980 |
| tcgaatcgag accatccgat ccaatctcat ccacgcacac aactcaagta aacgagaaac | 2040 |
| caaagatcaa aataaaaaaa aaatccccac gggctcttgt gttgtgttgt gtctcgagtc | 2100 |

```
gaggtctcgc ctgagtcgcc tctccctccc gagtctcctc tcctctcctt ctcctctcct    2160
ctctcgtgct ctcgcaaaac cctagcccac ctcccctcc  acccacggat cc            2212

<210> SEQ ID NO 10
<211> LENGTH: 2575
<212> TYPE: DNA
<213> ORGANISM: Glycine max

<400> SEQUENCE: 10
ggtacccatt tttagcttag ggtcctctgt ttggccatga aacttgggta tatgttccaa      60
tgttatagag gcattagcat tgacaatctc aagggttaaa tgagcaaaac ccgcaatatc     120
tgctttagat ctatgatgaa ttgatgatcg caaagtcatg acacaaaggt gataatgagg     180
tgattggcga catatttgct ctaacaaact tgtgtgagag agaatggatt gaattggtgg     240
aacaaagaag cctaatgaaa tggataactg aaggagaata aagttgaga  aacttgcaag     300 tatcattttt ctcctaaact caaaacataa aggaagatta ttgaattgaa tcacttatta     360
taacatgcaa taatatgatt tattagagga atgacgctag tggtctatgt tttctaccat     420
ttttaggaaa tattttgacg gtttcctttg tattcgctaa cgaggtgaaa gtgtggccta     480
aatggttttg aattctaaat tattagcttt acaagcttgc aaattaggga cagaaaaata     540
ggtctctttt tttccatgaa cttttgtgtt tgggttaatc agaaaccaat taaatccatg     600
aaatcacaaa gagaccgcga gaattttaaa ttttaattat ggatgcaccg atttccctta     660
taaaaccatg cataccaatt gcagctacct atctatctat atctgtatta tatagtttca     720
attattaaat ttatatatag tatgatatac aattaactta gattttttt  tgacaaaaaa     780 tgcaattaac ttagatagta ttattaaaca ttatatttt  agaataaata tatttattaa     840
atttaataaa tacaatatat gtttattagc aatttcaaat aataagagaa ttcaatatac     900
tacaataaat atttaattcc aataaaataa taattcctaa atttaaaga  atcacaaaac     960 actaatgcaa ataatttttt tataaattat aagtatttta aatttttttt attgtaaaaa    1020
aaacacaaaa ttgcattagt gacagagtta aggatagata aagggttgaa acttaaaagt    1080
tgaaatggaa aattacttaa cgcagaacaa tatttgcttg ggtgcaccat aattgcattc    1140
cggattgagt ccatatataa tacttataac atggattgtc caatttataa tacaattgtg    1200
gtgcagcaaa gcaaatacta tggtgcttta agtaattaac gttgaaatgg cagaatttga    1260
taaacagaca ctaaaaatac tgaaaggccg agataaggaa ggagtgagtg ggctaggtgg    1320
ctggaccagt aataataaaa ataaaaaggc tgtttctatt tacacctcaa tttttctggaa   1380 gtacatccct ctaccccttt ctactatcca ttataccctt ttctcttaaa gatgtacatt    1440
cattttcctc tttgaaaatg tattttttgga attaaatata tctattcccg aaatatatct    1500
ccaaaactat aatttatagt tctagagata cacttccaaa atggtataca ttattctaaa    1560
aggacatttt cgataataaa aaatcatacc aatcaaagta cttaagagtt ttcgagggtt    1620
gaggcctgaa taattgacat agacttggat tataaaatga atgaacatac ttaaaagaaa    1680
aaaccattgt caaaagcttt actttacaaa tacaatgtat aatagatgaa attaatcatg    1740 aacataccctt gaaacatagt gtcacatgaa ggaaaacact aaatattaca tgttctggat    1800
gaaaaaacaa tattatataa ttaatatatg gtgaaaatgg tttaaaatca aggtttaaag    1860
aataataaag atagtatgaa aataaaattt tagataggat ttaaataatc ccaatgatag    1920
gataaaaata agactaacaa acatgagtaa aagataaaca tttatctcgt taatatatat    1980
```

```
atttttttgt atttctcatt aacgatctta attttaaat gatatttat taaaatcat    2040 atacctattt cgaaagtata tctttgaaac tataaatgat agttataagt atatttaatt   2100
ttgaaaatat atttagtgta catctttaag ggagaagagt atagttggag ttatgagggt   2160
gtacctagcg aaaggagtg taaatagcaa gagcctaaga aaaatgctcc cgcaaaaaca    2220
aaacaaaaca aacacgagat actttcttcg tcgtcgtcgt ctcattcgtg agtagtattt   2280
atgaattatg aatttatgat tgtgttgtgt ctagtggtgc atagcagcgt aagccagaaa   2340
gacaagaggt gtcactccac cggagcaaag gaacacataa cataacccac ttctcctttt   2400
ctctctctct ctctctcact ataggttttc tgttagggtt ccgctctgtt aagccaagct   2460
ggatagacac agaggagaac gttacaacaa caacaatgat tttcacaaca acaataataa   2520
ctatcgtcac tccaacaggg ggggcaacaa ctctcactcg cgcttctctg gatcc         2575
```

<210> SEQ ID NO 11
<211> LENGTH: 1967
<212> TYPE: DNA
<213> ORGANISM: Artificial Sequence
<220> FEATURE:
<223> OTHER INFORMATION: Synthetic

<400> SEQUENCE: 11

```
ggatccaaca tgtatgatca ttttaacagc ccgagcattg atattctgta tgattatggc    60
ccgtttctga agaaatgcga atgaccggg ggcattggca gctatagcgc gggcaccccg   120
accccgcgcg tggcgattgt gggagcgggc attagcggcc tggtggcggc gaccgaactg   180
ctgcgcgctg gcgtgaaaga tgtggtgctg tatgaaagcc gcgatcgcat ggcggtcgc    240 gtgtggagcc aggtgtttga tcagacccgc ccacgctata ttgcggaaat gggcgcgatg   300 cgcttccgc cgagcgcgac cggcctgttt cattatctga agaagttcgg cattagcacc   360
agcaccacct ttcctgatcc gggcgtggtg ataccgaac tgcattatcg cggcaaacgc   420
tatcattggc cagcgggcaa gaaaccgccg gaactgtttc gccgcgtgta tgaaggctgg   480
cagagcctgc tgagcgaagg ctatctgctg gaaggcggca gcctggtggc gcctctggat   540
attaccgcga tgctgaaaag cggccgcctg gaagaagcgg cgattgcgtg gcagggctgg   600
ctgaacgtgt ttcgcgattg cagcttctat aacgcgattg tgtgcatctt caccggccgc   660
catccgcctg gcggcgatcg ctgggctcgc ccggaagatt tcgaactgtt tggcagcctg   720
ggcattggca gcggtggctt tctgccggtg tttcaggcgg gctttaccga gattctgcgc   780
atggtgatta acggctatca gagcgatcag cgcctgattc cggatggcat tagcagcctg   840
gcggctcgcc tggcggatca gagctttgat ggcaaagcgc tgcgcgatcg cgtgtgctttt   900 agccgcgtgg gccgcattag ccgcgaagcg gaaaagatca tcattcagac cgaagcgggc   960
gaacagcgcg tgttcgatcg cgtgattgtg accagcagca accgcgcgat gcagatgatt  1020
cattgcctga ccgatagcga gagctttctg agccgcgatg tggcacgcgc ggtgcgcgaa  1080
acccatctga ccggcagcag caaactgttc attctgaccc gcaccaagtt ctggatcaag  1140
aacaagctgc cgaccaccat tcagagcgat ggcctggtgc gcggcgtgta ttgcctggat  1200
tatcagccga tgaaccgga aggccatggc gtggtgctgc tgagctatac ctgggaagat  1260
gatgcgcaga agatgctggc gatgccggat aagaagaccc gctgccaggt gctggtggat  1320
gatctggcgg cgattcatcc gacctttgcg agctatctgc tgccggtgga tggcgattat  1380
gaacgctatg tgctgcatca tgattggctg accgatccgc atagcgcggg tgcgttcaag  1440
ctgaactatc cgggcgaaga tgtgtatagc cagcgcctgt tcttccagcc gatgaccgcg  1500
```

```
aacagcccga acaaagatac cggcctgtat ctggcgggct gcagctgcag ctttgcgggc    1560
ggctggattg aaggcgcggt gcagaccgcg ctgaacagcg cgtgcgcggt gctgcgcagc    1620
accggcggcc agctgagcaa aggcaacccg ctggattgca tcaacgcgag ctatcgctat    1680
taagagctcg agctcgatcg ttcaaacatt tggcaataaa gtttcttaag attgaatcct    1740
gttgccggtc ttgcgatgat tatcatataa tttctgttga attacgttaa gcatgtaata    1800
attaacatgt aatgcatgac gttatttatg agatgggttt ttatgattag agtcccgcaa    1860
ttatacattt aatacgcgat agaaaacaaa atatagcgcg caaactagga taaattatcg    1920
cgcgcggtgt catctatgtt actagatccc taggggtac caagctt                  1967

<210> SEQ ID NO 12
<211> LENGTH: 1968
<212> TYPE: DNA
<213> ORGANISM: Artificial Sequence
<220> FEATURE:
<223> OTHER INFORMATION: Synthetic

<400> SEQUENCE: 12
ggatccaaca atggacaagg gcagcgctgg cagcttcccg accatcgacc tgctgtacga      60
ctacaggccg ttcttcgacc agtgcagcga cagcggcagg atcggcttct cccggagga     120 cgtgccgaag ccgaaggtgg ccgtgatcgg agcggcatc agcggcctgg tggtggccaa     180
cgagctgctg cacgctggcg tggacgacgt gaccatctac gaggccagcg acagggtggg    240
tggcaagctg tggagccacg ccttcaggga cgccccaagc gtggtggccg agatgggcgc    300
catgaggttc ccacctgccg ccttctgcct gttcttcttc ctggagaggt acggcctgag    360
cagcatgagg ccgttcccga accctggcac cgtggacacc tacctggtgt accagggcgt    420
gcagtacatg tggaaggctg ccagctgcc tccgaagctg ttccacaggg tgtacaacgg     480
ctggagggcc ttcctgaagg acggcttcca cgagagggac atcgtgctgg ccagcccggt    540
ggccatcacc caggccctga gagcggcga catcaggtgg gcccacgaca gctggcaaat    600
ctggctgaac aggttcggca gggagagctt cagcagcggc atcgagagga tcttcctggg    660
cacccaccct ccaggtggcg agacctggag cttcccgcac gactgggacc tgttcaagct    720
gatgggcatc ggcagcggtg gcttcggccc ggtgttcgag agcggcttca tcgagatcct    780
gaggctggtg atcaacggct acgaggagaa ccagaggatg tgccctgagg catcagcga    840 gctgccgagg aggatcgcca gcgaggtggt gaacggcgtg agcgtgagcc agaggatctg    900
ccacgtgcag gtgagggcca tccagaagga gaagaccaag atcaagatca ggctgaagag    960
cggcatcagc gagctgtacg acaaggtggt ggtgaccagc ggcctggcca acatccagct   1020
gaggcactgc ctgacctgcg acaccaacat cttccaggcc ctgtgaacc aggccgtgga   1080 caacagccac atgaccggca gcagcaagct gttcctgatg accgagagga gttctggct    1140 ggaccacatc ctgccgagct gcgtgctgat ggacggcatc gccaaggccg tgtactgcct   1200
ggactacgag agccaggacc cgaacggcaa gggcctggtg ctgatcagct acacctggga   1260
ggacgacagc cacaagctgc tggccgtgcc ggacaagaag gagaggctgt gcctgctgag   1320
ggacgccatc agcaggagct cccagccctt cgcccagcac ctgttcccag cctgcgccga   1380
ctacgaccag aacgtgatcc agcacgactg gctgaccgac gagaacgctg cggtgccctt   1440
caagctgaac aggaggggcg aggacttcta cagcgaggag ctgttcttcc aggccctgga   1500
caccgccaac gacacaggcg tgtacctggc tggttgcagc tgcagcttca ccggtggctg   1560
```

| | |
|---|---|
| ggtggaggga gccatccaga ccgcctgcaa cgccgtgtgc gccatcatcc acaactgcgg | 1620 |
| aggcatcctg gccaagggca acccgctgga gcacagctgg aagaggtaca actacaggac | 1680 |
| caggaactaa gagctcgatc gttcaaacat ttggcaataa agtttcttaa gattgaatcc | 1740 |
| tgttgccggt cttgcgatga ttatcatata atttctgttg aattacgtta agcatgtaat | 1800 |
| aattaacatg taatgcatga cgttatttat gagatgggtt tttatgatta gagtcccgca | 1860 |
| attatacatt taatacgcga tagaaaacaa aatatagcgc gcaaactagg ataaattatc | 1920 |
| gcgcgcggtg tcatctatgt tactagatcc ctaggggta ccaagctt | 1968 |

<210> SEQ ID NO 13
<211> LENGTH: 1516
<212> TYPE: DNA
<213> ORGANISM: Artificial Sequence
<220> FEATURE:
<223> OTHER INFORMATION: Synthetic

<400> SEQUENCE: 13

| | |
|---|---|
| ggatccaaca atggacaaca agccggccca ggagaggagg gagacctggg tgccgggcgc | 60 |
| cgtgatcgtg ggcgccggcc cgagcggcct ggccgccgcc gcctgcctgg ccgccagggg | 120 |
| cgtgccggcc accgtgctgg agaggagcga cagcctggcc agcacctgga ggcacaggat | 180 |
| gtacgacagg ctggccctgc acctgccgaa gaggttctgc gagctgccgc tgctgccgtt | 240 |
| cccggaggag tacccgacct acccgagcaa ggaccagttc gtggcctaca tggaggccta | 300 |
| cgccgccgcc gccggcgtgg ccccgaggtt cggcgccacc gtggaggagg ccgccttcga | 360 |
| cgccgccgtg ggcgcctgga gggtgaggct ggacggcggc gaggtgctga tggccaggtg | 420 |
| gctggtggtg gccaccggcg agaacgccga gccgagggtg ccggacttcc cgggcatgca | 480 |
| gaagttcgcc ggctgcgcca tgcacaccag cgagtacaag agcggcgagc agttcgccgg | 540 |
| caagaaggtg ctggtggtgg gctgcggcaa cagcggcatg gaggtgagcc tggacctgtg | 600 |
| caggcacggc gccaagccga gcatggtggt gaggaacacc gtgcacgtgc tgccgaggga | 660 |
| gatgttcggc ctgagcacct cggcatcgc catggccctg ctgaggtggc tgccgatcca | 720 |
| gctggtggac aggttcctgc tgaccgccgc ccacctgatc ctgggcaaca ccggccagtt | 780 |
| cggcctgagg aggccgaaga ccggcccgat cgagctgaag aacctgaccg gcaggacccc | 840 |
| ggtgctggac gtgggcaccc tggaccacat caagagcggc aagatcaagg tggtgggcgc | 900 |
| cgtgaaggag atgaccaggc agggcgtgag gttcaccgac ggcaaggagg agcagttcga | 960 |
| caccatcatc ctggccaccg gctacaggag caacgtgccg agctggctga aggacgccgg | 1020 |
| cgacctgttc accagggagg gcatcagcaa ggtgccgttc ccgaacagct ggaggggcag | 1080 |
| gaacggcctg tacaccgtgg gcttcaccca gaggggcctg ctgggcacca gcagcgacgc | 1140 |
| cctgaacgtg gccaaggaca tccactgcca gtggagggag agggacagga gcgccatcaa | 1200 |
| cgtgctggag atcagcaaca gcagcttcta aagagctcga gctcgatcgt tcaaacattt | 1260 |
| ggcaataaag tttcttaaga ttgaatcctg ttgccggtct tgcgatgatt atcatataat | 1320 |
| ttctgttgaa ttacgttaag catgtaataa ttaacatgta atgcatgacg ttatttatga | 1380 |
| gatgggtttt tatgattaga gtcccgcaat tatacattta atacgcgata gaaaacaaaa | 1440 |
| tatagcgcgc aaactaggat aaattatcgc gcgcggtgtc atctatgtta ctagatccct | 1500 |
| aggggtacc aagctt | 1516 |

<210> SEQ ID NO 14
<211> LENGTH: 557

<212> TYPE: PRT
<213> ORGANISM: Peudomonas syringae

<400> SEQUENCE: 14

```
Met Tyr Asp His Phe Asn Ser Pro Ser Ile Asp Ile Leu Tyr Asp Tyr
  1               5                  10                  15

Gly Pro Phe Leu Lys Lys Cys Glu Met Thr Gly Gly Ile Gly Ser Tyr
             20                  25                  30

Ser Ala Gly Thr Pro Thr Pro Arg Val Ala Ile Val Gly Ala Gly Ile
         35                  40                  45

Ser Gly Leu Val Ala Ala Thr Glu Leu Leu Arg Ala Gly Val Lys Asp
     50                  55                  60

Val Val Leu Tyr Glu Ser Arg Asp Arg Ile Gly Gly Arg Val Trp Ser
 65                  70                  75                  80

Gln Val Phe Asp Gln Thr Arg Pro Arg Tyr Ile Ala Glu Met Gly Ala
                 85                  90                  95

Met Arg Phe Pro Pro Ser Ala Thr Gly Leu Phe His Tyr Leu Lys Lys
            100                 105                 110

Phe Gly Ile Ser Thr Ser Thr Thr Phe Pro Asp Pro Gly Val Val Asp
            115                 120                 125

Thr Glu Leu His Tyr Arg Gly Lys Arg Tyr His Trp Pro Ala Gly Lys
            130                 135                 140

Lys Pro Pro Glu Leu Phe Arg Arg Val Tyr Glu Gly Trp Gln Ser Leu
145                 150                 155                 160

Leu Ser Glu Gly Tyr Leu Leu Glu Gly Gly Ser Leu Val Ala Pro Leu
                165                 170                 175

Asp Ile Thr Ala Met Leu Lys Ser Gly Arg Leu Glu Glu Ala Ala Ile
            180                 185                 190

Ala Trp Gln Gly Trp Leu Asn Val Phe Arg Asp Cys Ser Phe Tyr Asn
            195                 200                 205

Ala Ile Val Cys Ile Phe Thr Gly Arg His Pro Pro Gly Gly Asp Arg
            210                 215                 220

Trp Ala Arg Pro Glu Asp Phe Glu Leu Phe Gly Ser Leu Gly Ile Gly
225                 230                 235                 240

Ser Gly Gly Phe Leu Pro Val Phe Gln Ala Gly Phe Thr Glu Ile Leu
                245                 250                 255

Arg Met Val Ile Asn Gly Tyr Gln Ser Asp Gln Arg Leu Ile Pro Asp
            260                 265                 270

Gly Ile Ser Ser Leu Ala Ala Arg Leu Ala Asp Gln Ser Phe Asp Gly
            275                 280                 285

Lys Ala Leu Arg Asp Arg Val Cys Phe Ser Arg Val Gly Arg Ile Ser
290                 295                 300

Arg Glu Ala Glu Lys Ile Ile Ile Gln Thr Glu Ala Gly Glu Gln Arg
305                 310                 315                 320

Val Phe Asp Arg Val Ile Val Thr Ser Ser Asn Arg Ala Met Gln Met
                325                 330                 335

Ile His Cys Leu Thr Asp Ser Glu Ser Phe Leu Ser Arg Asp Val Ala
            340                 345                 350

Arg Ala Val Arg Glu Thr His Leu Thr Gly Ser Ser Lys Leu Phe Ile
            355                 360                 365

Leu Thr Arg Thr Lys Phe Trp Ile Lys Asn Lys Leu Pro Thr Thr Ile
            370                 375                 380

Gln Ser Asp Gly Leu Val Arg Gly Val Tyr Cys Leu Asp Tyr Gln Pro
385                 390                 395                 400
```

Asp Glu Pro Glu Gly His Gly Val Val Leu Leu Ser Tyr Thr Trp Glu
                405                 410                 415

Asp Asp Ala Gln Lys Met Leu Ala Met Pro Asp Lys Lys Thr Arg Cys
            420                 425                 430

Gln Val Leu Val Asp Asp Leu Ala Ala Ile His Pro Thr Phe Ala Ser
        435                 440                 445

Tyr Leu Leu Pro Val Asp Gly Asp Tyr Glu Arg Tyr Val Leu His His
    450                 455                 460

Asp Trp Leu Thr Asp Pro His Ser Ala Gly Ala Phe Lys Leu Asn Tyr
465                 470                 475                 480

Pro Gly Glu Asp Val Tyr Ser Gln Arg Leu Phe Phe Gln Pro Met Thr
                485                 490                 495

Ala Asn Ser Pro Asn Lys Asp Thr Gly Leu Tyr Leu Ala Gly Cys Ser
            500                 505                 510

Cys Ser Phe Ala Gly Gly Trp Ile Glu Gly Ala Val Gln Thr Ala Leu
        515                 520                 525

Asn Ser Ala Cys Ala Val Leu Arg Ser Thr Gly Gly Gln Leu Ser Lys
    530                 535                 540

Gly Asn Pro Leu Asp Cys Ile Asn Ala Ser Tyr Arg Tyr
545                 550                 555

<210> SEQ ID NO 15
<211> LENGTH: 567
<212> TYPE: PRT
<213> ORGANISM: Agrobacterium tumefaciens

<400> SEQUENCE: 15

Met Val Ala Tyr Gly Arg Asn Leu Met Leu Lys Gly Ser Ala Gly Ser
1               5                   10                  15

Phe Pro Thr Ile Asp Leu Leu Tyr Asp Tyr Arg Pro Phe Phe Asp Gln
            20                  25                  30

Cys Ser Asp Ser Gly Arg Ile Gly Phe Phe Pro Glu Asp Val Pro Lys
        35                  40                  45

Pro Lys Val Ala Val Ile Gly Ala Gly Ile Ser Gly Leu Val Val Ala
    50                  55                  60

Asn Glu Leu Leu His Ala Gly Val Asp Asp Val Thr Ile Tyr Glu Ala
65                  70                  75                  80

Ser Asp Arg Val Gly Gly Lys Leu Trp Ser His Ala Phe Arg Asp Ala
                85                  90                  95

Pro Ser Val Val Ala Glu Met Gly Ala Met Arg Phe Pro Pro Ala Ala
            100                 105                 110

Phe Cys Leu Phe Phe Phe Leu Glu Arg Tyr Gly Leu Ser Ser Met Arg
        115                 120                 125

Pro Phe Pro Asn Pro Gly Thr Val Asp Thr Tyr Leu Val Tyr Gln Gly
    130                 135                 140

Val Gln Tyr Met Trp Lys Ala Gly Gln Leu Pro Pro Lys Leu Phe His
145                 150                 155                 160

Arg Val Tyr Asn Gly Trp Arg Ala Phe Leu Lys Asp Gly Phe His Glu
                165                 170                 175

Arg Asp Ile Val Leu Ala Ser Pro Val Ala Ile Thr Gln Ala Leu Lys
            180                 185                 190

Ser Gly Asp Ile Arg Trp Ala His Asp Ser Trp Gln Ile Trp Leu Asn
        195                 200                 205

Arg Phe Gly Arg Glu Ser Phe Ser Ser Gly Ile Glu Arg Ile Phe Leu

Gly Thr His Pro Pro Gly Glu Thr Trp Ser Phe Pro His Asp Trp
225                 230                 235                 240

Asp Leu Phe Lys Leu Met Gly Ile Gly Ser Gly Phe Gly Pro Val
                245                 250                 255

Phe Glu Ser Gly Phe Ile Glu Ile Leu Arg Leu Val Ile Asn Gly Tyr
            260                 265                 270

Glu Glu Asn Gln Arg Met Cys Pro Gly Ile Ser Glu Leu Pro Arg
            275                 280                 285

Arg Ile Ala Ser Glu Val Val Asn Gly Val Ser Val Ser Gln Arg Ile
290                 295                 300

Cys His Val Gln Val Arg Ala Ile Gln Lys Glu Lys Thr Lys Ile Lys
305                 310                 315                 320

Ile Arg Leu Lys Ser Gly Ile Ser Glu Leu Tyr Asp Lys Val Val Val
                325                 330                 335

Thr Ser Gly Leu Ala Asn Ile Gln Leu Arg His Cys Leu Thr Cys Asp
                340                 345                 350

Thr Asn Ile Phe Gln Ala Pro Val Asn Gln Ala Val Asp Asn Ser His
            355                 360                 365

Met Thr Gly Ser Ser Lys Leu Phe Leu Met Thr Glu Arg Lys Phe Trp
370                 375                 380

Leu Asp His Ile Leu Pro Ser Cys Val Leu Met Asp Gly Ile Ala Lys
385                 390                 395                 400

Ala Val Tyr Cys Leu Asp Tyr Glu Ser Gln Asp Pro Asn Gly Lys Gly
                405                 410                 415

Leu Val Leu Ile Ser Tyr Thr Trp Glu Asp Ser His Lys Leu Leu
                420                 425                 430

Ala Val Pro Asp Lys Lys Glu Arg Leu Cys Leu Leu Arg Asp Ala Ile
            435                 440                 445

Ser Arg Ser Phe Pro Ala Phe Ala Gln His Leu Phe Pro Ala Cys Ala
450                 455                 460

Asp Tyr Asp Gln Asn Val Ile Gln His Asp Trp Leu Thr Asp Glu Asn
465                 470                 475                 480

Ala Gly Gly Ala Phe Lys Leu Asn Arg Arg Gly Glu Asp Phe Tyr Ser
                485                 490                 495

Glu Glu Leu Phe Phe Gln Ala Leu Asp Thr Ala Asn Asp Thr Gly Val
            500                 505                 510

Tyr Leu Ala Gly Cys Ser Cys Ser Phe Thr Gly Gly Trp Val Glu Gly
            515                 520                 525

Ala Ile Gln Thr Ala Cys Asn Ala Val Cys Ala Ile Ile His Asn Cys
530                 535                 540

Gly Gly Ile Leu Ala Lys Gly Asn Pro Leu Glu His Ser Trp Lys Arg
545                 550                 555                 560

Tyr Asn Tyr Arg Thr Arg Asn
                565

<210> SEQ ID NO 16
<211> LENGTH: 571
<212> TYPE: PRT
<213> ORGANISM: Dickeya dadantii

<400> SEQUENCE: 16

Met Leu Thr Phe Trp Gly Gly Tyr Met Ser Asn Asp Ala Ser Phe Leu
1               5                   10                  15

-continued

```
Ala Asn Ser Val Pro Cys Val Asp Leu Leu Tyr Asp Tyr Ala Pro Phe
            20                  25                  30
Leu Gln Cys Ser Glu Ala Glu Gly Arg Ile Gly Tyr Phe Pro Pro Gly
        35                  40                  45
Ile Pro Thr Pro Arg Val Ala Ile Ile Gly Ala Gly Ile Ser Gly Leu
    50                  55                  60
Val Ala Ala Thr Glu Leu Leu Arg Ala Gly Val Lys Asp Ile Thr Leu
65                  70                  75                  80
Phe Glu Ala Arg Asp Arg Arg Ile Gly Gly Arg Val Trp Ser Gln Thr
                85                  90                  95
Phe Asp Pro Arg Tyr Pro His Leu Ile Ala Glu Met Gly Ala Met Arg
            100                 105                 110
Phe Pro Ser Ser Glu Thr Cys Leu Phe Tyr Tyr Leu Asn Lys Leu Asp
        115                 120                 125
Ile Ala Thr Thr Thr Ser Phe Pro Asp Pro Gly Val Val Asp Thr Glu
    130                 135                 140
Leu His Tyr Arg Gly Val Arg His Ile Trp Ser Ala Gly Asp Pro Pro
145                 150                 155                 160
Pro Ser Leu Phe Ser Arg Val His Glu Gly Trp Val Ala Leu Leu Asn
                165                 170                 175
Glu Gly Tyr Leu His Asn Gly Val Pro Leu Val Ala Pro Arg Asp Ile
            180                 185                 190
Thr Ala Met Leu Lys Ser His Cys Phe Asp Lys Ala Arg Lys Ala Trp
        195                 200                 205
Gln Ala Trp Leu Asp Ala Phe Arg Asp Tyr Ser Phe Tyr Ser Ala Leu
    210                 215                 220
Val Thr Met Phe Thr Ser Asn Thr Pro Pro Gly Gly Val Pro Trp Arg
225                 230                 235                 240
Arg Pro Asp Asp Phe Glu Leu Phe Gly Ser Leu Gly Ile Gly Ser Gly
                245                 250                 255
Gly Phe Leu Pro Val Tyr Gln Ala Gly Phe Thr Glu Ile Leu Arg Leu
            260                 265                 270
Val Ile Asn Gly Tyr Glu Asp Asp Gln Arg Leu Ile Ile Gly Gly Ile
        275                 280                 285
Ser Thr Leu Ala Glu Arg Leu Val Ser Gln Lys Ile Gly Asp Thr Arg
    290                 295                 300
Leu Ser Glu His Ile Cys Phe Asn Glu Val Lys Arg Ile Tyr Lys Glu
305                 310                 315                 320
Asp Gly Glu Ile Lys Leu Val Ser Gly Lys Gly Gln Thr His Thr Phe
                325                 330                 335
Asp Arg Val Ile Val Thr Ser Ser Thr Arg Thr Met Gln Ile Val His
            340                 345                 350
Cys Leu Thr Gly Asp Glu Thr Phe Leu Glu His Asp Ile Ser Arg Ala
        355                 360                 365
Val Lys Glu Thr His Leu Thr Gly Ser Ser Lys Leu Phe Met Leu Thr
    370                 375                 380
Arg Asn Lys Phe Trp Leu Asn Asp Ser Leu Pro Val Thr Ile Gln Ser
385                 390                 395                 400
Asp Gly Phe Ile Arg Gly Val Tyr Cys Leu Asp Tyr Glu Pro Asp Asn
                405                 410                 415
Pro Asp Gly Pro Gly Val Val Leu Leu Ser Tyr Thr Trp Glu Asp Asp
            420                 425                 430
Ala His Lys Leu Leu Ser Ile Pro Asp Lys Lys Gln Arg Cys Gln Tyr
```

```
                      435                 440                 445
Leu Val Asp Asp Leu Ala Lys Ile Asn Pro Glu Phe Ala Arg His Leu
450                 455                 460
Ile Pro Ala Asp Gly Asp Tyr Glu Arg Tyr Val Leu His His Asp Trp
465                 470                 475                 480
Leu Val Asp Pro Tyr Ser Ala Gly Ala Phe Lys Leu Asn Tyr Pro Gly
                485                 490                 495
Glu Asp Val Tyr Ser Gln Arg Leu Phe Phe Gln Phe Lys Asn Ala Asn
                500                 505                 510
Thr Pro Glu Lys Asp Thr Gly Leu Tyr Leu Ala Gly Cys Gly Cys Ser
                515                 520                 525
Phe Thr Gly Gly Trp Ile Glu Gly Ala Met Gln Thr Ala Leu Asn Ser
530                 535                 540
Ala Cys Ala Val Ile Arg Ser Ser Gly Gly Ala Leu Leu Val Gly Asn
545                 550                 555                 560
Pro Leu Asp Asp Met His Ser Ala Tyr Cys Tyr
                565                 570

<210> SEQ ID NO 17
<211> LENGTH: 562
<212> TYPE: PRT
<213> ORGANISM: Pantoea agglomerans

<400> SEQUENCE: 17

Met Lys Pro His Ser Val Phe Ala Asp Ser Leu Trp Pro Ser Ile Asp
1               5                   10                  15
Leu Leu Tyr Asp Tyr Ala Pro Phe Leu Gln Gln Ser Met Val Asp Gly
                20                  25                  30
His Ile Gly Phe Phe Pro Thr Gly Ile Thr Pro Pro Arg Val Ala Ile
            35                  40                  45
Ile Gly Ala Gly Ile Ser Gly Leu Ile Ala Ala Thr Glu Leu Leu Arg
    50                  55                  60
Ala Gly Val Arg Asp Ile Thr Leu Phe Glu Ala Arg Asp Arg Leu Gly
65                  70                  75                  80
Gly Arg Ala Trp Ser Gln Leu Phe Asp Pro His Tyr Tyr Pro Arg Leu
                85                  90                  95
Ile Ala Glu Met Gly Ala Met Arg Phe Pro Pro Ser Ala Thr Gly Leu
                100                 105                 110
Phe His Tyr Leu Asn Arg Phe Ser Ile Gln Thr Ser Ala Ser Phe Pro
            115                 120                 125
Asp Pro Gly Ile Val Asp Thr Glu Leu His Tyr Arg Gly Val Arg His
    130                 135                 140
Leu Trp Pro Ala Gly Glu Gln Pro Pro Ala Leu Phe Thr Arg Val His
145                 150                 155                 160
Asn Gly Trp Arg Ala Leu Leu Tyr Glu Gly Cys Leu Leu Asp Gly Val
                165                 170                 175
Ser Leu Val Gly Pro Leu Gln Ile Thr Ala Met Leu Lys Ser Glu Arg
                180                 185                 190
Phe Asp Glu Ala Ala Glu Ala Trp Gln Ile Trp Leu Asn Val Phe Arg
            195                 200                 205
Asp Cys Ser Phe Tyr Ser Ala Met Val Thr Ile Phe Thr Gly Thr Asn
    210                 215                 220
Pro Pro Gly Gly Ile Ala Trp Glu Arg Arg Asp Asp Phe Glu Leu Phe
225                 230                 235                 240
```

```
Gly Ala Leu Gly Ile Gly Ser Gly Gly Phe Leu Pro Val Tyr Gln Ala
                245                 250                 255

Gly Phe Thr Glu Ile Leu Arg Met Val Ile Asn Gly Tyr Glu Asp Asp
            260                 265                 270

Gln Arg Leu Ile Ile Gly Gly Ile Ser Thr Leu Ala Glu Gln Leu Ala
        275                 280                 285

Arg Gln Glu Ile Arg Gly Thr Thr Pro Gly Arg His Val Arg Phe Ser
290                 295                 300

Lys Val Asn Arg Ile Ser Lys Asp Asn Gly Lys Ile Ser Leu Ala Thr
305                 310                 315                 320

Asp Val Lys Pro Val Asp Ala Phe Asp Arg Val Ile Val Thr Ser Asn
                325                 330                 335

Asn Arg Ala Met Gln Met Val His Gly Leu Ser Ala Asp Glu Thr Phe
            340                 345                 350

Leu Asn Gln Asp Val Cys Arg Ala Val Arg Glu Thr His Leu Thr Gly
        355                 360                 365

Ser Ser Lys Leu Phe Met Leu Thr Arg Asp Lys Phe Trp Leu Lys Asn
370                 375                 380

Lys Leu Pro Leu Thr Ile Gln Ser Asp Gly Leu Val Arg Gly Val Tyr
385                 390                 395                 400

Val Leu Asp Tyr Glu Ser Asp Asn Pro Glu Gly Arg Gly Val Val Leu
                405                 410                 415

Leu Ser Tyr Thr Trp Glu Asp Ala His Lys Leu Leu Ala Ile Thr
            420                 425                 430

Asp Lys Lys Gln Arg Gly Gln His Leu Val Asp Glu Leu Ser Ala Ile
        435                 440                 445

His Pro Glu Phe Ala Arg Tyr Leu Val Pro Ala Gly Ala Asp Tyr Glu
450                 455                 460

Arg Tyr Val Leu His His Asp Trp Leu Thr Asp Pro Cys Ser Ala Gly
465                 470                 475                 480

Ala Phe Lys Leu Asn Tyr Pro Gly Glu Asp Val Tyr Ser Gln Arg Leu
                485                 490                 495

Phe Phe Gln Phe Lys Thr Ala Asn His Pro Glu Gln Asp Ser Gly Leu
            500                 505                 510

Leu Leu Ala Gly Cys Gly Cys Ser Phe Thr Gly Gly Trp Val Glu Gly
        515                 520                 525

Ala Val Gln Thr Ala Val Asn Ser Ala Cys Ala Val Ile Arg Ser Thr
530                 535                 540

Gly Gly Thr Leu Tyr Gly Asn Pro Leu Asp Ser Val His Ser Ile Tyr
545                 550                 555                 560

Asp Tyr

<210> SEQ ID NO 18
<211> LENGTH: 567
<212> TYPE: PRT
<213> ORGANISM: Agrobacterium vitis

<400> SEQUENCE: 18

Met Val Ala Tyr Gly Arg Asn Leu Met Leu Lys Ala Ser Ala Gly Ser
1               5                   10                  15

Phe Pro Thr Ile Asp Leu Leu Tyr Asp Tyr Arg Leu Phe Leu Asp Lys
            20                  25                  30

Cys Ser Asp Ser Gly Arg Ile Gly Phe Phe Pro Glu Asp Val Pro Arg
        35                  40                  45
```

```
Pro Lys Val Ala Val Ile Gly Ala Gly Ile Ser Gly Leu Val Val Ala
    50                  55                  60

Ser Glu Leu Leu His Ala Gly Val Asp Asp Val Thr Ile Tyr Glu Ala
65                  70                  75                  80

Gly Asp Arg Val Gly Gly Lys Leu Trp Ser His Ala Phe Lys Asp Ala
                85                  90                  95

Pro Gly Val Val Ala Glu Met Gly Ala Met Arg Phe Pro Pro Ala Ala
            100                 105                 110

Ser Cys Leu Phe Phe Phe Leu Glu Arg Tyr Gly Leu Ser Ser Met Arg
            115                 120                 125

Pro Phe Pro Asn Pro Gly Thr Val Asp Thr Asp Leu Val Tyr Glu Gly
    130                 135                 140

Cys Arg Tyr Met Trp Lys Ala Gly Gln Gln Pro Pro Lys Leu Phe His
145                 150                 155                 160

Arg Val Tyr Ser Gly Trp His Ala Phe Leu Lys Asp Gly Phe Leu Glu
                165                 170                 175

Gly Asp Ile Val Leu Ala Ser Pro Asp Ala Ile Thr Glu Ala Leu Lys
            180                 185                 190

Ser Gly Asp Ile Arg Arg Ala His Asp Ser Trp Gln Ile Trp Leu Asn
            195                 200                 205

Arg Phe Gly Arg Glu Ser Phe Ser Ser Ala Ile Glu Arg Ile Phe Leu
    210                 215                 220

Gly Thr His Pro Pro Gly Gly Glu Thr Trp Ser Phe Pro His Asp Trp
225                 230                 235                 240

Asp Leu Phe Lys Leu Met Gly Ile Gly Ser Gly Gly Phe Gly Pro Val
                245                 250                 255

Phe Glu Ser Gly Phe Thr Glu Ile Leu Arg Leu Val Ile Asn Gly Tyr
            260                 265                 270

Glu Glu Asn Gln Arg Met Cys Ser Glu Gly Ile Ser Glu Leu Pro Arg
            275                 280                 285

Arg Ile Ala Ser Gln Val Val Asn Gly Val Ser Val Ser Gln Arg Ile
    290                 295                 300

Arg His Val Gln Val Arg Ala Ile Glu Lys Glu Lys Thr Lys Ile Lys
305                 310                 315                 320

Ile Arg Leu Lys Ser Gly Ile Ser Glu Leu Tyr Asp Lys Val Val Val
                325                 330                 335

Thr Ser Gly Leu Ala Asn Ile Gln Leu Arg His Cys Leu Thr Cys Asp
            340                 345                 350

Thr Thr Ile Phe Arg Ala Pro Val Asn Gln Ala Val Asp Asn Ser His
            355                 360                 365

Met Thr Gly Ser Ser Lys Leu Phe Leu Leu Thr Glu Arg Lys Phe Trp
    370                 375                 380

Phe Asp His Met Leu Pro Ser Cys Val Leu Met Asp Gly Phe Ala Lys
385                 390                 395                 400

Ala Val Tyr Cys Leu Asp Tyr Glu Pro Gln Asp Pro Asn Gly Lys Gly
                405                 410                 415

Leu Val Leu Ile Ser Tyr Thr Trp Glu Asp Asp Ser His Lys Leu Leu
            420                 425                 430

Ala Val Pro Asp Lys Lys Glu Arg Leu Cys Leu Leu Arg Asp Ala Ile
            435                 440                 445

Ser Lys Ser Phe Pro Val Phe Ala Gln His Leu Val Pro Ala Cys Ala
    450                 455                 460

Asp Tyr Asp Gln Asn Val Val Gln His Asp Trp Leu Thr Asp Glu Asn
```

```
                465                 470                 475                 480
Ala Gly Gly Arg Phe Lys Leu Asn Arg Arg Gly Glu Asp Phe Tyr Ser
                    485                 490                 495

Glu Glu Leu Phe Phe Gln Ala Leu Asp Thr Thr Asn Asp Thr Gly Val
                500                 505                 510

Tyr Leu Ala Gly Cys Ser Cys Ser Phe Thr Gly Gly Trp Val Glu Gly
                515                 520                 525

Ala Ile Gln Thr Ala Cys Asn Ala Val Cys Ala Ile Ile His Asn Cys
                530                 535                 540

Gly Gly Ile Leu Ala Lys Asp Asn Pro Leu Lys His Pro Trp Lys Arg
545                 550                 555                 560

Tyr Asn Tyr Arg Asn Arg Asn
                565

<210> SEQ ID NO 19
<211> LENGTH: 414
<212> TYPE: PRT
<213> ORGANISM: Arabidopsis thaliana

<400> SEQUENCE: 19

Met Glu Ser His Pro His Asn Lys Thr Asp Gln Thr Gln His Ile Ile
1               5                   10                  15

Leu Val His Gly Pro Ile Ile Gly Ala Gly Pro Ser Gly Leu Ala
                20                  25                  30

Thr Ser Ala Cys Leu Ser Ser Arg Gly Val Pro Ser Leu Ile Leu Glu
                35                  40                  45

Arg Ser Asp Ser Ile Ala Ser Leu Trp Lys Ser Lys Thr Tyr Asp Arg
50                  55                  60

Leu Arg Leu His Leu Pro Lys His Phe Cys Arg Leu Pro Leu Leu Asp
65                  70                  75                  80

Phe Pro Glu Tyr Tyr Pro Lys Tyr Pro Ser Lys Asn Glu Phe Leu Ala
                85                  90                  95

Tyr Leu Glu Ser Tyr Ala Ser His Phe Arg Ile Ala Pro Arg Phe Asn
                100                 105                 110

Lys Asn Val Gln Asn Ala Ala Tyr Asp Ser Ser Ser Gly Phe Trp Arg
                115                 120                 125

Val Lys Thr His Asp Asn Thr Glu Tyr Leu Ser Lys Trp Leu Ile Val
                130                 135                 140

Ala Thr Gly Glu Asn Ala Asp Pro Tyr Phe Pro Glu Ile Pro Gly Arg
145                 150                 155                 160

Lys Lys Phe Ser Gly Gly Lys Ile Val His Ala Ser Glu Tyr Lys Ser
                165                 170                 175

Gly Glu Glu Phe Arg Arg Gln Lys Val Leu Val Val Gly Cys Gly Asn
                180                 185                 190

Ser Gly Met Glu Ile Ser Leu Asp Leu Val Arg His Asn Ala Ser Pro
                195                 200                 205

His Leu Val Val Arg Asn Thr Val His Val Leu Pro Arg Glu Ile Leu
                210                 215                 220

Gly Val Ser Thr Phe Gly Val Gly Met Thr Leu Leu Lys Cys Leu Pro
225                 230                 235                 240

Leu Arg Leu Val Asp Lys Phe Leu Leu Leu Met Ala Asn Leu Ser Phe
                245                 250                 255

Gly Asn Thr Asp Arg Leu Gly Leu Arg Arg Pro Lys Thr Gly Pro Leu
                260                 265                 270
```

-continued

```
Glu Leu Lys Asn Val Thr Gly Lys Ser Pro Val Leu Asp Val Gly Ala
            275                 280                 285

Met Ser Leu Ile Arg Ser Gly Met Ile Gln Ile Met Glu Gly Val Lys
        290                 295                 300

Glu Ile Thr Lys Lys Gly Ala Lys Phe Met Asp Gly Gln Glu Lys Asp
305                 310                 315                 320

Phe Asp Ser Ile Ile Phe Ala Thr Gly Tyr Lys Ser Asn Val Pro Thr
                325                 330                 335

Trp Leu Gln Gly Gly Asp Phe Phe Thr Asp Asp Gly Met Pro Lys Thr
                340                 345                 350

Pro Phe Pro Asn Gly Trp Arg Gly Gly Lys Gly Leu Tyr Thr Val Gly
            355                 360                 365

Phe Thr Arg Arg Gly Leu Leu Gly Thr Ala Ser Asp Ala Val Lys Ile
        370                 375                 380

Ala Gly Glu Ile Gly Asp Gln Trp Arg Asp Glu Ile Lys Gly Ser Thr
385                 390                 395                 400

Arg Asn Met Cys Ser Ser Arg Phe Val Phe Thr Ser Lys Ser
                405                 410

<210> SEQ ID NO 20
<211> LENGTH: 39
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)...(39)
<223> OTHER INFORMATION: pOsTE1-F

<400> SEQUENCE: 20
aagcttgaaa ctagtactag acattactct tccaatgca                              39

<210> SEQ ID NO 21
<211> LENGTH: 35
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)...(35)
<223> OTHER INFORMATION: pOsTE1-R

<400> SEQUENCE: 21
agaggatcct gcagcagcac ttacctaccc tacca                                  35

<210> SEQ ID NO 22
<211> LENGTH: 23
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)...(23)
<223> OTHER INFORMATION: OsTE-PRO-DELF

<400> SEQUENCE: 22
agatccgagc aaaaaacagg gcc                                               23

<210> SEQ ID NO 23
<211> LENGTH: 33
<212> TYPE: DNA
```

```
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)...(33)
<223> OTHER INFORMATION: OsTE-PRO-DEL

<400> SEQUENCE: 23
tctatagcga tagaactgtt tgatctgggt agc                           33

<210> SEQ ID NO 24
<211> LENGTH: 35
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)...(35)
<223> OTHER INFORMATION: pZmTE1-F

<400> SEQUENCE: 24
agaaagctta gtgccaatca ctgcgtgaga accga                         35

<210> SEQ ID NO 25
<211> LENGTH: 32
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)...(32)
<223> OTHER INFORMATION: pZmTE1-R

<400> SEQUENCE: 25
aggggatcct ccactccctc ccccaccctc ca                            32

<210> SEQ ID NO 26
<211> LENGTH: 40
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)...(40)
<223> OTHER INFORMATION: pGmTE 1 -F

<400> SEQUENCE: 26
aggaagcttg aaagaacgta gtcccttctt aaaaatggtg                    40

<210> SEQ ID NO 27
<211> LENGTH: 40
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)...(40)
<223> OTHER INFORMATION: pGmTE1-R

<400> SEQUENCE: 27
aggggatcct caaatctcac tcactcgcct cttttcctca                    40

<210> SEQ ID NO 28
<211> LENGTH: 28
```

```
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)...(28)
<223> OTHER INFORMATION: pAtTE 1 -F

<400> SEQUENCE: 28
aggaagctta cttcgtgttt aacaaaca                                              28

<210> SEQ ID NO 29
<211> LENGTH: 32
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)...(32)
<223> OTHER INFORMATION: pAtTE 1 -R

<400> SEQUENCE: 29
aggggatcct aataccagag ttgatagggg cc                                         32

<210> SEQ ID NO 30
<211> LENGTH: 30
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)...(30)
<223> OTHER INFORMATION: pAtMl1-F

<400> SEQUENCE: 30
agaaagctta cttagcccta tgagcttaac                                            30

<210> SEQ ID NO 31
<211> LENGTH: 29
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)...(29)
<223> OTHER INFORMATION: pAtMl1- R

<400> SEQUENCE: 31
agaggatcca aacccaaatt gcctctgcc                                             29

<210> SEQ ID NO 32
<211> LENGTH: 24
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)...(24)
<223> OTHER INFORMATION: pBrTE1-F

<400> SEQUENCE: 32
aagcttccca aatttaatcg aacc                                                  24

<210> SEQ ID NO 33
```

```
<211> LENGTH: 27
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)...(27)
<223> OTHER INFORMATION: pBrTE1-R

<400> SEQUENCE: 33
ggatccttta attattttct tacggga                                27

<210> SEQ ID NO 34
<211> LENGTH: 26
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)...(26)
<223> OTHER INFORMATION: pOsFCA-F

<400> SEQUENCE: 34
aagctttgag ggatgttagg tctcga                                 26

<210> SEQ ID NO 35
<211> LENGTH: 27
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)...(27)
<223> OTHER INFORMATION: pOsFCA-R

<400> SEQUENCE: 35
ggatccgtgg gtggaggggg aggtggg                                27
```

USE OF AUXIN SYNTHASE FOR IMPROVING CROP YIELD

CROSS-REFERENCE TO RELATED APPLICATIONS

This application is the U.S. National Stage of International Application PCT/CN2012/087542 filed Dec. 26, 2012, which designates the U.S. and was published by the International Bureau in English on Jul. 4, 2013, and which claims the benefit of Chinese Application No. 201110450964.2, filed Dec. 29, 2011, both of which are hereby incorporated by reference in their entirety.

FIELD OF THE INVENTION

This invention is in the field of plant genetic engineering. This invention involves a method of obtaining high-yield transgenic plants by expressing indoleacetic acid (IAA) synthase gene in plants. This invention can be applied in the field of crop breeding.

BACKGROUND OF THE INVENTION

Auxin is an important signal chemical that controls plant growth and development. It controls plant cell division, expansion and differentiation, as well as lateral root formation and flowering. (Davies P. J. (2004) *The Plant Hormone: Their Nature*, Kluwer, Dordrecht, the Netherlands). The biosynthetic pathway of auxin at the genetic level has remained unclear. Two major pathways have been proposed: The tryptophan(Try)-independent and Trp-dependent pathways. See, Mashiguchi et al. (2011) *PNAS* 108:18512-18517). There are also auxin synthase genes in microorganisms (Thomashow et al. (1984) *PNAS* 81:5071-5075; Van Onckelen et al. (1986) *FEBS Lett* 198:357-360. Although the research on auxin is very extensive, the synthesis pathways and the function of auxin remain unclear in plants.

In recent years, the auxin synthase gene has been used as a tool for crop improvement. The auxin synthase gene has been expressed in the epithelial cells of cotton ovule resulting in transgenic cotton with traits of high quality and high yield. (Zhang et al. (2011) *Nature Biotechnology* 29: 453-458). The auxin synthase gene was also expressed in grape driven by the ovule-specific promoter resulting in the increase in grape fecundity. (Costantini et al. (2007) *Plant Physiol* 143:1689-1694). However, there are still no effective methods to improve the yield of major crops, such as rice, corn, soybean, wheat, barley, sorghum and sunflower. The impact of auxin on plants is complicated. In fact, excess auxin can be highly harmful to plant. Therefore, methods are needed to utilize auxin to enhance crop yield.

SUMMARY OF INVENTION

Compositions and methods for increasing plant yield are provided. The methods of the invention comprise increasing the expression of an auxin synthase gene or coding sequence in the shoot meristem and inflorescence of a plant. Compositions of the invention comprise DNA constructs comprising an auxin synthase coding sequence operably linked to a promoter that drives expression in the shoot meristem and inflorescence of a plant. Also encompassed are plants, plant cells, plant tissues, and seeds that have been transformed with the DNA construct. The invention recognizes that enhancing the expression of auxin in the shoot meristem and inflorescence of a plant results in an improvement in plant yield, resulting in an increase in crop yield in a field planted with such plants.

Thus, the present invention relates generally to the field of molecular biology and concerns a method for increasing plant yield relative to control plants. More specifically, the present invention concerns a method for increasing plant yield comprising modulating expression of a nucleic acid molecule encoding an auxin synthase gene or a homologue thereof in the shoot meristem and inflorescence of a plant. The present invention also concerns plants having elevated expression of a nucleic acid encoding the auxin synthase gene in shoot meristems and inflorescence, which plants have increased growth and yield relative to control plants. The invention also provides constructs useful in the methods of the invention.

The following embodiments are encompassed by the present invention:

1. A method for increasing plant yield in a plant of interest, said method comprising transforming said plant with a DNA construct comprising a promoter that drives expression in a plant shoot meristem and inflorescence operably linked to an auxin synthase coding sequence, and selecting plants having a high yield phenotype.
2. The method of embodiment 1, wherein said promoter is a promoter from a plant Mei2-like gene.
3. The method of embodiment 2, wherein said promoter comprises a sequence selected from the sequences set forth in SEQ ID NO:1-SEQ ID NO:10.
4. The method of any one of embodiments 1-3, wherein said auxin synthase coding sequence is an indoleacetic acid (IAA) synthase coding sequence from a microorganism.
5. The method of any one of embodiments 1-3, wherein said auxin synthase coding sequence is a plant auxin synthase coding sequence.
6. The method of any one of embodiments 4 or 5, wherein said auxin synthase coding sequence is a synthetic sequence.
7. The method of any one of embodiments 1-3 and 5, wherein said auxin synthase coding sequence is selected from the group consisting of:
   i) the sequence set forth in SEQ ID NO:11, 12, or 13;
   ii) a sequence having at least 60% sequence identity to the sequence set forth in SEQ ID NO:11, 12, or 13;
   iii) a nucleotide sequence that encodes the amino acid sequence set forth in any one of SEQ ID NOs:14-19; and,
   iv) a nucleotide sequence that encodes an amino acid sequence having at least 40% sequence identity to any one of SEQ ID NOs:14-19.
8. The method of any one of embodiments 1-7, wherein plant is selected from the group consisting of rice, corn, cotton, wheat, barley, soybean, sunflower, canola, and sorghum.
9. An expression cassette comprising a DNA construct, said construct comprising a promoter that drives expression in a plant shoot meristem and inflorescence operably linked to an auxin synthase coding sequence.
10. The expression cassette of embodiment 9, wherein said promoter is a promoter from a plant Mei2-like gene.
11. The expression cassette of any one of embodiments 9-10, wherein said promoter comprises a sequence selected from the sequences set forth in SEQ ID NO:1-SEQ ID NO:10.
12. The expression cassette of any one of embodiments 9-11, wherein said auxin synthase coding sequence is an indoleacetic acid (IAA) synthase coding sequence from a microorganism.

13. The expression cassette of any one of embodiments 9-11, wherein said auxin synthase coding sequence is a plant auxin synthase coding sequence.
14. The expression cassette of any one of embodiments 12 or 13, wherein said auxin synthase coding sequence is a synthetic sequence.
15. The expression cassette of any one of embodiments 9-11 and 13, wherein said auxin synthase coding sequence is selected from the group consisting of:
   i) the sequence set forth in SEQ ID NO:11, 12, or 13;
   ii) a sequence having at least 60% sequence identity to the sequence set forth in SEQ ID NO:11, 12, or 13;
   iii) a nucleotide sequence that encodes the amino acid sequence set forth in any one of SEQ ID NOs:14-19; and,
   iv) a nucleotide sequence that encodes an amino acid sequence having at least 40% sequence identity to any one of SEQ ID NOs:14-19.
16. A plant transformed with the expression cassette of any one of embodiments 9-12.
17. A transformed seed of the plant of embodiment 16.
18. The method of any one of embodiments 5, wherein said auxin synthase sequence is an endogenous sequence.
19. A transformed plant that exhibits increased expression of auxin synthase in its shoot meristem and inflorescence as compared to a control plant.
20. The transformed plant of embodiment 19, wherein said plant has been transformed with a DNA construct comprising a promoter that drives expression in a plant shoot meristem and inflorescence operably linked to an auxin synthase coding sequence.
21. The transformed plant of embodiment 19 or 20, wherein said plant wherein said promoter is a promoter from a plant Mei2-like gene.
22. The transformed plant of embodiment 21, wherein said promoter comprises a sequence selected from the sequences set forth in SEQ ID NO:1-SEQ ID NO:10.
23. The transformed plant of any one of embodiments 19-22 wherein said auxin synthase coding sequence is an indoleacetic acid (IAA) synthase coding sequence from a microorganism.
24. The transformed plant of any one of embodiments 19-22, wherein said auxin synthase coding sequence is a plant auxin synthase coding sequence.
25. The transformed plant of any one of embodiments 19-24, wherein said auxin synthase coding sequence is a synthetic sequence.
26. The transformed of any one of embodiments 19-22 and 24-25, wherein said auxin synthase coding sequence is selected from the group consisting of:
   i) the sequence set forth in SEQ ID NO:11, 12, or 13;
   ii) a sequence having at least 60% sequence identity to the sequence set forth in SEQ ID NO:11, 12, or 13;
   iii) a nucleotide sequence that encodes the amino acid sequence set forth in any one of SEQ ID NOs:14-19; and,
   iv) a nucleotide sequence that encodes an amino acid sequence having at least 40% sequence identity to any one of SEQ ID NOs:14-19.
27. The transformed plant of embodiment 24, wherein said auxin synthase coding sequence is an endogenous sequence.
28. Transformed seed from the plant of any one of embodiments 19-27.
29. The transgenic plant of any one of embodiments 19-27, wherein said plant is selected from the group consisting of rice, corn, cotton, wheat, barley, soybean, sunflower, canola, and sorghum.
30. The plant of any one of embodiments 19-27, wherein said plant is a monocot.
31. The plant of any one of embodiments 19-27, wherein said plant is a dicot.
32. A transformed plant having increased expression of auxin synthase in shoot meristem or inflorescence and further having increased expression of a TEL sequence.

DETAILED DESCRIPTION

The present invention is drawn to methods for increasing the expression of an auxin synthase gene or coding sequence in the shoot meristem and inflorescence of plants or plant cells. By increasing or enhancing the expression of an auxin synthase in the shoot meristem and inflorescence, the plant exhibits an improvement in plant yield. Expression in the plant is increased by transforming the plant with a DNA construct comprising a promoter that drives expression in the shoot meristem and inflorescence of a plant operably linked to an auxin synthase coding sequence.

An increase in the expression of an auxin synthase sequence in the shoot meristem and inflorescence of a plant results in an increase in plant growth and yield. The transformed plant has an increase in yield with no reduction in harvest index. Transformed plants have increased seed production and larger seed. Some plants may exhibit increased growth with larger plants resulting. Planting a field of transformed plants of the invention will result in increased crop yield. By "crop yield" is intended the amount of a crop that is harvested per unit of land area. Crop yield is the measurement often used for a cereal, grain, or legume and is normally measured in metric tons per hectare (or kilograms per hectare). Crop yield also refers to the actual seed generation from the plant.

By "enhancing or increasing the expression of an auxin synthase gene or coding sequence" is intended that the expression as measured by the production of mRNA or auxin synthase protein is increased in the plant of interest as compared to a control plant. Auxin synthase is increased at least about 0.25-fold, at least about 0.3-fold, at least about 0.5-fold, at least about one-fold, at least about two-fold, at least about three-fold, at least about four-fold, at least about five-fold, at least about six-fold, at least about seven-fold, at least about eight-fold, at least about nine-fold, at least about 10-fold or greater.

By "control plant" is intended a plant where the expression of auxin synthase sequence has not been altered or enhanced, i.e., a plant or plant cell genetically identical to the subject plant or plant cell but which is not exposed to conditions or stimuli that would increase expression of an auxin synthase sequence.

While not bound by any theory, it is believed that extreme over-production of the auxin synthase coding sequence may result in plants with undesirable phenotypes. Therefore, one can control expression by the selection of the promoters used to drive expression of an auxin synthase sequence in a transformed plant. Tissue-preferred promoters, particularly, those promoters that are preferentially expressed in the early stage of flower development are preferred in the invention. Such promoters should not be strong promoters. Promoters that drive expression in the shoot meristem and inflorescence are useful in the practice of the invention. Such promoters include Mei2 promoters. The Mei2 promoters provide good results in expressing the recombinant gene at desired levels and in desired tissues. As discussed below, any promoter that drives expression in the shoot meristem and inflorescence of a plant may be used. Once a plant has been transformed, one can select the desired plant based on the phenotype. Thus, the methods of the invention further comprise selection of the desired phenotype of the transformed plant. Such desired plants will exhibit increased growth and yield of grain or biomass.

Such desired plants can be grown and crossed with suitable plants to produce seed having the desired phenotype. That is, the recombinant auxin synthase gene that has been inserted into the genome of a plant can be bred into other plants. Such plants will be grown and used to produce a crop with enhanced yield.

By "auxin synthase gene" or "auxin synthase sequence" is intended a sequence that encodes the entire amino acid sequence of the auxin synthase protein or variants or truncations of the auxin synthase protein. A number of auxin synthase genes are known in the art and any can be used in the practice of the invention, including fragments and variants of known auxin synthase genes as long as the fragments and variants retain the desired activity of promoting plant growth and increasing yield. Any auxin synthase coding sequence can be used in the practice of the invention. The auxin synthase gene can come from either a microorganism or a plant. For example, the microbial auxin synthase genes include but are not limited are: auxin synthases from *Agrobacterium tumefaciens* (AAF77123, AAB41874), auxin synthases from *Pseudomonas syringae* (AAR06971, EF100478, and AAA17678), auxin synthase from *Dickeya dadantii* (ADM96599), auxin synthase from *Pantoea agglomerans* (AAC17187), etc. Auxin synthases from plant may be also used in the practice of the invention. Such auxin synthase sequences include, for example, auxin synthase (CAB79971) from *Arabidopsis thaliana* and its homologous genes in other plants. Other auxin synthases can be isolated or cloned from other plants and microorganisms using the above identified sequences. Likewise, auxin synthase sequences can be synthesized artificially. The advantage of the synthetic DNA fragment is the amino acid codons usage can be optimized for different target plants. The methods of the invention are not limited to any particular auxin synthase. Thus, other auxin synthases from other organisms can also be utilized for the purpose of this invention.

The auxin synthase or auxin synthase-like proteins include those having at least 40%, at least 50%, at least 58% at least 60%, at least 70%, at least 80%, at least 90%, at least 91%, at least 92%, at least 93%, at least 94%, at least 95%, at least 96%, at least 97%, at least 98%, at least 99% sequence identity to a known auxin synthase sequence.

A number of auxin synthase genes are disclosed herein and are known in the art and any of these auxin synthase sequences, as well as variants and truncations thereof, can be used in any plant of interest. As discussed below, the sequences herein can be used to isolate other auxin synthase genes that are useful in the practice of the invention. Nucleotide sequences encoding the auxin synthase proteins of the present invention include the sequences set forth in SEQ ID NOs: 11-13, and variants, fragments, and complements thereof.

Nucleic acid molecules that are fragments of these nucleotide sequences encoding auxin synthase proteins are also encompassed by the present invention. By "fragment" is intended a portion of the nucleotide sequence encoding an auxin synthase protein. A fragment of a nucleotide sequence may encode a biologically active portion of an auxin synthase protein, or it may be a fragment that can be used as a hybridization probe or PCR primer useful for isolating other auxin synthase-like sequences. Typically, truncations fragments of the nucleotide sequences of the present invention will encode protein fragments that retain the biological activity of the auxin synthase protein and, hence, retain auxin synthase activity. By "retains activity" is intended that the fragment will have at least about 50%, at least about 70%, 80%, 90%, 95% or higher of the auxin synthase activity of the auxin synthase protein. By "auxin synthase activity" is intended the production of ethylene production and increased plant growth or yield. Those plants exhibiting the desired levels of increased auxin synthase production can be selected based on the phenotype of the regenerated plant. Thus, variants and truncations of the auxin synthase sequence can be tested for activity by transformation of the sequence in a plant of interest and selecting for plants having the desired phenotype.

Variants of the auxin synthase nucleic acid molecules may be made by various methods. These alterations may result in DNA sequences encoding proteins with amino acid sequences different than that encoded by an auxin synthase protein of the present invention. Thus, the protein may be altered in various ways including amino acid substitutions, deletions, truncations, and insertions of one or more amino acids. Methods for such manipulations are generally known in the art.

Preferred auxin synthase proteins of the present invention are encoded by a nucleotide sequence identical or having sequence identity to the nucleotide sequence of any of the auxin synthase sequences listed herein or contained within the sequence listing. Variant amino acid or nucleotide sequences having at least about 40%, about 50%, about 60% or 65% sequence identity, about 70% or 75% sequence identity, about 80% or 85% sequence identity, about 90%, 91%, 92%, 93%, 94%, 95%, 96%, 97%, 98%, 99% or greater sequence identity compared to a reference auxin synthase sequence using one of the alignment programs described herein using standard parameters are encompassed by the invention. Auxin synthase proteins of the present invention include the sequences set forth in SEQ ID NOs: 14-19, and variants, fragments, and complements thereof. One of skill in the art will recognize that these values can be appropriately adjusted to determine corresponding identity of proteins encoded by two nucleotide sequences by taking into account codon degeneracy, amino acid similarity, reading frame positioning, and the like.

The determination of percent identity between two sequences can be accomplished using a mathematical algorithm. A nonlimiting example of a mathematical algorithm utilized for the comparison of two sequences is the algorithm of Karlin and Altschul (1990) *Proc. Natl. Acad. Sci. USA* 87:2264, modified as in Karlin and Altschul (1993) *Proc. Natl. Acad. Sci. USA* 90:5873-5877. Such an algorithm is incorporated into the BLASTN and BLASTX programs of Altschul et al. (1990) *J. Mol. Biol.* 215:403. BLAST nucleotide searches can be performed with the BLASTN program, score=100, wordlength=12, to obtain nucleotide sequences homologous to auxin synthase-like nucleic acid molecules of the invention. BLAST protein searches can be performed with the BLASTX program, score=50, wordlength=3, to obtain amino acid sequences homologous to auxin synthase protein molecules of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., BLASTX and BLASTN) can be used. Alignment may also be performed manually by inspection.

Other mathematical algorithms may be used for the comparison of sequences including the ClustalW algorithm (Higgins et al. (1994) *Nucleic Acids Res.* 22:4673-4680). Unless otherwise stated, GAP Version 10, which uses the algorithm of Needleman and Wunsch (1970) *J. Mol. Biol.* 48(3):443-453, will be used to determine sequence identity or similarity using the following parameters: % identity and % similarity for a nucleotide sequence using GAP Weight of 50 and Length Weight of 3, and the nwsgapdna.cmp scoring matrix; % identity or % similarity for an amino acid sequence using GAP weight of 8 and length weight of 2, and the BLOSUM62 scoring program. Equivalent programs may also be used. By "equivalent program" is intended any sequence comparison program that, for any two sequences in question, generates an alignment having identical nucleotide residue matches and an identical percent sequence identity when compared to the corresponding alignment generated by GAP Version 10.

As indicated, variant auxin synthase nucleic acid molecules may be used in the practice of the invention. "Variants" of the auxin synthase protein encoding nucleotide sequences include those sequences that encode the auxin synthase proteins disclosed herein but that differ conservatively because of the degeneracy of the genetic code as well as those that are sufficiently identical as discussed above. Naturally occurring allelic variants can be identified with the use of well-known molecular biology techniques, such as polymerase chain reaction (PCR) and hybridization techniques as outlined below. Variant nucleotide sequences also include synthetically derived nucleotide sequences that have been generated, for example, by using site-directed mutagenesis but which still encode the auxin synthase proteins disclosed in the present invention as discussed below. Variant proteins encompassed by the present invention are biologically active, that is they continue to possess the desired biological activity of the native protein, that is, auxin synthase activity.

The skilled artisan will further appreciate that changes can be introduced by mutation of the nucleotide sequences of the invention thereby leading to changes in the amino acid sequence of the encoded auxin synthase proteins, without altering the biological activity of the proteins. Thus, variant isolated nucleic acid molecules can be created by introducing one or more nucleotide substitutions, additions, or deletions into the corresponding nucleotide sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleotide sequences are also encompassed by the present invention.

For example, conservative amino acid substitutions may be made at one or more, predicted, nonessential amino acid residues. A "nonessential" amino acid residue is a residue that can be altered from the wild-type sequence of an auxin synthase protein without altering the biological activity, whereas an "essential" amino acid residue is required for biological activity. A "conservative amino acid substitution" is one in which the amino acid residue is replaced with an amino acid residue having a similar side chain.

Amino acid substitutions may be made in nonconserved regions that retain function. In general, such substitutions would not be made for conserved amino acid residues, or for amino acid residues residing within a conserved motif, where such residues are essential for protein activity. Examples of residues that are conserved and that may be essential for protein activity include, for example, residues that are identical between all proteins contained in an alignment of similar or related proteins to the sequences of the invention (e.g., residues that are identical in an alignment of homologous proteins). However, one of skill in the art would understand that functional variants may have minor conserved or nonconserved alterations in the conserved residues. In one embodiment, changes in the amino acid sequence will not be made in the conserved motifs or in the region surrounding the motifs as set forth in Figure 2.

Antibodies to the polypeptides of the present invention, or to variants or fragments thereof, are also encompassed. Methods for producing antibodies are well known in the art (see, for example, Harlow and Lane (1988) *Antibodies: A Laboratory Manual*, Cold Spring Harbor Laboratory, Cold Spring Harbor, N.Y.; U.S. Pat. No. 4,196,265).

In addition to the auxin synthase proteins listed in this application, this invention also provides methods to clone and utilize new auxin synthase genes from other organisms, including plants, moss, microorganisms, and fungi. For example, by using the sequences provided herein, one can clone new auxin synthase genes using methods such as PCR and nucleic acid hybridization. PCR primers may be designed according to the conservative regions of the DNA sequences of auxin synthase genes. Moreover, the conservative amino acid sequences may be used to design degenerate primers for PCR. A partially known gene from PCR can be used to clone a full-length gene using various known methods, such as Tail-PCR, 5'RACE, 3'RACE, etc. See, for example, Singer and Burke (2003) *Methods Mol Biol* 236: 241-272; and commercially available kits. As described below, the genes provided in this invention and in other publications can be used to prepare probes to hybridize genomic or cDNA libraries to clone auxin synthase genes.

With the rapid advancement of various sequencing projects, new auxin synthase genes may be identified by searching various databases using the auxin synthase amino acid sequences and/or nucleic sequences provided by this invention. Such databases include but not limited to databases of genome sequence, ETS, and cDNA sequences. BLAST method (Altschul et al. 1990 J. Mol. Biol. 215, 403-410) is a wide used.

In a hybridization method, all or part of an auxin synthase nucleotide sequence disclosed herein can be used to screen cDNA or genomic libraries for additional auxin synthase sequences for use in the invention. Methods for construction of such cDNA and genomic libraries are generally known in the art and are disclosed in Sambrook and Russell, 2001, supra. The so-called hybridization probes may be genomic DNA fragments, cDNA fragments, RNA fragments, or other oligonucleotides, and may be labeled with a detectable group such as $^{32}P$, or any other detectable marker, such as other radioisotopes, a fluorescent compound, an enzyme, or an enzyme co-factor. Methods for the preparation of probes for hybridization are generally known in the art and are disclosed in Sambrook and Russell, 2001, supra herein incorporated by reference.

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m=81.5°$ C.$+16.6(\log M)+0.41(\% GC)-0.61(\% form)-500/L$; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Cold Spring Harbor, N.Y.).

As noted above, methods of the invention comprise transforming a plant of interest with a DNA construct or expression cassette comprising a nucleic acid molecule that encodes an auxin synthase sequence of the invention. The expression cassette will include in the 5'-3' direction of transcription, a transcriptional and translational initiation region (i.e., a promoter), a DNA sequence of the invention, and a translational and transcriptional termination region (i.e., termination region) functional in plants. General methods to introduce and express an auxin synthase gene in a plant and hence crops are currently available. As indicated, an auxin synthase sequence of the invention may be provided in a DNA construct or an expression cassette for expression in a plant of interest. By "plant expression cassette" is intended a DNA construct that is capable of resulting in the expression of a protein from an open reading frame in a plant cell. Typically these contain a promoter and a coding sequence. Often, such constructs will also contain a 3' untranslated region.

By "plant transformation vector" is intended a DNA molecule that is necessary for efficient transformation of a plant cell. Such a molecule may consist of one or more plant expression cassettes, and may be organized into more than one "vector" DNA molecule. For example, binary vectors are plant transformation vectors that utilize two non-contiguous DNA vectors to encode all requisite cis- and trans-acting functions for transformation of plant cells (Hellens and Mullineaux (2000) *Trends in Plant Science* 5:446-451). "Vector" refers to a nucleic acid construct designed for transfer between different host cells. "Expression vector" refers to a vector that has the ability to incorporate, integrate and express heterologous DNA sequences or fragments in a foreign cell. The cassette will include 5' and 3' regulatory sequences operably linked to a sequence of the invention. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. The cassette may additionally contain at least one additional gene to be cotransformed into the organism. Alternatively, the additional gene(s) can be provided on multiple expression cassettes.

"Promoter" refers to a nucleic acid sequence that functions to direct transcription of a downstream coding sequence. The promoter together with other transcriptional and translational regulatory nucleic acid sequences (also termed "control sequences") are necessary for the expression of a DNA sequence of interest. Promoters for use in the practice of the invention include those that drive expression in the shoot meristem and inflorescence of a plant. Promoters are of critical importance for this invention. The promoters used by this invention to control the auxin synthase gene are the ones which can regulate the gene express preferentially in plant shoot meristem and inflorescence, and in low to very low expression levels. An example of a promoter for use in the invention includes the promoter from the plant TEL gene. This type of promoter has the following characteristics: a) they are the promoters of plant TEL gene (for instance, NP_594609 and CAA15822); and, b) they regulate the expression specifically in plant shoot meristem and inflorescence. These promoters including the promoter from *Oryza sativa* (SEQ ID NO: 1); from *Zea mays* (SEQ ID NO: 2); from *Glycine max* (SEQ ID NOs:3, 4); from *Arabidopsis thaliana* (SEQ ID NOs: 5-7); and from *Brassica rapa* (SEQ ID NO: 8). Since the function and specificity of expression of a promoter in different plants are normally conservative, the promoter from one plant often has the same or similar function in another plant. Thus, the promoters provided by this invention may be used in different plants. Promoters to regulate the auxin synthase genes for higher yield can be other promoters, such as the promoters of the FCA gene of *Arabidopsis thaliana* and its homologous promoters from other plants. These promoters including the promoter from *Oryza sativa* (SEQ ID NO: 9) and from *Glycine max* (SEQ ID NOs:10).

Other meristem-and-inflorescence specific promoters can be obtained by general molecular biology methods. For example, by sequencing the mRNA from a plant inflorescence, the genes expressed in the inflorescence can be obtained. The expression specificities of these genes can be determined by gene chip or Northern blot. Genes expressed in the inflorescence, especially in the early inflorescence, may be obtained by general molecular biological techniques. After the genome of a plant was sequenced, the regions of promoters can be determined by molecular informatics methods and cloned. Normally, the promoter of a gene often locates on the 5' end of the coding region of the protein in the genome, which has a length within about 2-3 kb.

The DNA constructs of the invention may further comprise a terminator. The frequently-used terminators include the octopine synthase terminator and nopaline synthase terminator from *Agrobacterium*. See, for example, Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639. Besides, other terminators can also be used in the plant expression cassette. This invention provides an example (Example 2) in which the auxin synthase gene and the terminator were simultaneously synthesized, which simplified the construction procedure of the expression cassette.

The DNA construct or expression cassette is provided with a plurality of restriction sites for insertion of the auxin synthase sequence to be under the transcriptional regulation of the regulatory regions.

Methods of the invention involve introducing a nucleotide construct into a plant. By "introducing" is intended to present to the plant the nucleotide construct in such a manner that the construct gains access to the interior of a cell of the plant. The methods of the invention do not require that a particular method for introducing a nucleotide construct to a plant is used, only that the nucleotide construct gains access to the interior of at least one cell of the plant. Methods for introducing nucleotide constructs into plants are known in the art including, but not limited to, stable transformation methods, transient transformation methods, and virus-mediated methods.

By "plant" is intended whole plants, plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells, pollen).

"Transgenic plants" or "transformed plants" or "stably transformed" plants or cells or tissues refers to plants that have incorporated or integrated exogenous nucleic acid sequences or DNA fragments into the plant cell. These nucleic acid sequences include those that are exogenous, or not present in the untransformed plant cell, as well as those that may be endogenous, or present in the untransformed plant cell. "Heterologous" generally refers to the nucleic acid sequences that are not endogenous to the cell or part of the native genome in which they are present, and have been added to the cell by infection, transfection, microinjection, electroporation, microprojection, or the like.

In general, plant transformation methods involve transferring heterologous DNA into target plant cells (e.g. immature or mature embryos, suspension cultures, undifferentiated callus, protoplasts, etc.), followed by applying appropriate selection (depending on the selectable marker gene) to recover the transformed plant cells from a group of untransformed cell mass. Explants are typically transferred to a fresh supply of the same medium and cultured routinely. Subsequently, the transformed cells are differentiated into shoots after placing on regeneration medium supplemented with a maximum threshold level of selecting agent. The shoots are then transferred to a selective rooting medium for recovering rooted shoot or plantlet. The transgenic plantlet then grows into a mature plant and produces fertile seeds (e.g. Hiei et al. (1994) *The Plant Journal* 6:271-282; Ishida et al. (1996) *Nature Biotechnology* 14:745-750). Explants are typically transferred to a fresh supply of the same medium and cultured routinely. A general description of the techniques and methods for generating transgenic plants are found in Ayres and Park (1994) *Critical Reviews in Plant Science* 13:219-239 and Bommineni and Jauhar (1997) *Maydica* 42:107-120. Since the transformed material contains many cells; both transformed and non-transformed cells are present in any piece of subjected target callus or tissue or group of cells. The ability to kill non-transformed cells and allow transformed cells to proliferate results in transformed plant cultures. Often, the ability to remove non-transformed cells is a limitation to rapid recovery of transformed plant cells and successful generation of transgenic plants.

Transformation protocols as well as protocols for introducing nucleotide sequences into plants may vary depending on the type of plant or plant cell, i.e., monocot or dicot, targeted for transformation. Generation of transgenic plants may be performed by one of several methods, including, but not limited to, microinjection (Crossway et al. (1986) Biotechniques 4:320 334), electroporation (Riggs et al. (1986) Proc. Natl. Acad. Sci. USA 83:5602 5606, *Agrobacterium*-mediated transformation (U.S. Pat. Nos. 5,563,055 and 5,981,840), direct gene transfer (Paszkowski et al. (1984) EMBO J. 3:2717 2722), and ballistic particle acceleration (see, for example, U.S. Pat. Nos. 4,945,050; 5,879,918; 5,886,244; and, 5,932,782; Tomes et al. (1995) in Plant Cell, Tissue, and Organ Culture: Fundamental Methods, ed. Gamborg and Phillips (Springer-Verlag, Berlin); McCabe et al. (1988) Biotechnology 6:923 926); and Lec1 transformation (WO 00/28058). Also see Weissinger et al. (1988) Ann. Rev. Genet. 22:421 477; Christou et al. (1988) Plant Physiol. 87:671 674; Datta et al. (1990) Biotechnology 8:736 740 (rice); Klein et al. (1988) Proc. Natl. Acad. Sci. USA 85:4305 4309; Klein et al. (1988) Biotechnology 6:559 563. See, also, U.S. Pat. Nos. 5,240,855; 5,322,783; 4,945,050; 5,324,646; U.S. Published Application No. 20010026941; 2002015066; and, International Publication No. WO 91/00915.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a nucleotide construct of the invention, for example, an expression cassette of the invention, stably incorporated into their genome.

Following introduction of heterologous foreign DNA into plant cells, the transformation or integration of heterologous gene in the plant genome is confirmed by various methods such as analysis of nucleic acids and proteins associated with the integrated gene. Molecular techniques include PCR (Sambrook and Russell (2001) Molecular Cloning: A Laboratory Manual. Cold Spring Harbor Laboratory Press, Cold Spring Harbor, N.Y.), Southern blot analysis of genomic DNA, Northern blot analysis and Western blot (Sambrook and Russell, 2001, supra).

A number of selectable markers have been developed for use with plant cells, such as resistance to chloramphenicol, the aminoglycoside G418, hygromycin, or the like. Other genes that encode a product involved in chloroplast metabolism may also be used as selectable markers. For example, genes that provide resistance to plant herbicides such as glyphosate, bromoxynil, or imidazolinone may find particular use. Such genes have been reported (Stalker et al. (1985) *J. Biol. Chem.* 263:6310-6314 (bromoxynil resistance nitrilase gene); and Sathasivan et al. (1990) *Nucl. Acids Res.* 18:2188 (AHAS imidazolinone resistance gene). Methods for detecting the presence of a transgene in a plant, plant organ (e.g., leaves, stems, roots, etc.), seed, plant cell, propagule, embryo or progeny of the same are well known in the art.

Fertile plants expressing an auxin synthase protein may be tested for auxin synthase activity, and the plants showing the desired phenotype selected for further breeding.

The methods of the invention can be used with other genes and methods for increasing yield. In one embodiment, the methods of the invention can be used in combination with methods to increase a TEL sequence for enhanced yield in the modified plants. Methods to increase plant growth and yield by increasing expression of a TEL sequence are set forth in PCT Application No. PCT/CN2012/087069, filed 20 Dec. 2012, entitled "Methods for Improving Crop Yield." The disclosure of which is herein incorporated by reference. Any method to increase the expression of a TEL sequence in the plant and to increase the expression of auxin synthase in the shoot meristem and inflorescence can be used. In one embodiment, a plant that has been modified to have increased expression of a TEL sequence can be transformed with a construct comprising an auxin synthase coding sequence operably linked to a promoter that drives expression in the shoot meristem and inflorescence and plants with the desired phenotype selected after transformation and selection.

In another embodiment, a plant that has increased expression of auxin synthase in shoot meristem and inflorescence can be modified to increase the expression of a TEL sequence. Expression of the TEL sequence can be increased by transforming the plant with a construct comprising a TEL coding sequence operably linked with a promoter that drives expression in a plant cell, or by transforming the plant with an enhancer that increases the expression of the endogenous TEL coding sequence. In another embodiment, a plant that has increased expression of auxin synthase in the shoot meristem and inflorescence can be crossed with a plant that has increased expression of a TEL sequence and plants selected that retain the increased expression of a TEL sequence and the increased expression of auxin synthase in shoot meristem and inflorescence.

The methods of the invention may be used in any plant species, including, but not limited to, monocots and dicots. Examples of plants of interest include, but are not limited to, corn (maize), sorghum, wheat, sunflower, tomato, crucifers, peppers, potato, cotton, rice, soybean, sugarbeet, sugarcane, tobacco, barley, and oilseed rape, *Brassica* sp., alfalfa, rye, millet, safflower, peanuts, sweet potato, cassava, coffee, coconut, pineapple, citrus trees, cocoa, tea, banana, avocado, fig, guava, mango, olive, papaya, cashew, macadamia, almond, oats, vegetables, ornamentals, and conifers.

Vegetables include, but are not limited to, tomatoes, lettuce, green beans, lima beans, peas, and members of the genus *Curcumis* such as cucumber, cantaloupe, and musk melon. Ornamentals include, but are not limited to, azalea, hydrangea, hibiscus, roses, tulips, daffodils, petunias, carnation, poinsettia, and chrysanthemum. Preferably, plants of the present invention are crop plants (for example, maize, sorghum, wheat, sunflower, tomato, crucifers, peppers, potato, cotton, rice, soybean, sugarbeet, sugarcane, tobacco, barley, oilseed rape, *Miscanthus*, switchgrass, *Jatropha*, etc.) and conifers.

The following examples are offered by way of illustration and not by way of limitation.

EXPERIMENTAL

Example 1

Cloning of the Promoters of Mei2-Like Genes from Rice, Corn, Soybean, Canola and *Arabidopsis thaliana*

(1) Cloning of Promoter pOsTE1 of Mei2-Like Gene from Rice

The 5' end sequence of OsTE1 was amplified by PCR using the designed primers pOsTE1-F (5'-AAGCTT-GAAACTAGTACTAGACATTACTCTTCCAATGCA; SEQ ID NO: 20) and pOsTE1-R (5'-AGAGGATCCTGCA-GCAGCACTTACCTACCCTACCA; SEQ ID NO: 21). The PCR conditions were: 95° C. for 5 min, then 30 cycles at 95° C. for 1min, 58° C. for 1 min, 72° C. for 1 min, then extend at 72° C. for 5 min. The resulting PCR product of about 2 Kb in length was cloned into T-vector pMD19 (TaKaRa). Further, the BamHI site inside the promoter was removed by point mutation using primers OsTE-PRO-DELF (5'-AGATCCGAGCAAAAAACAGGGCC; SEQ ID NO: 22) and OsTE-PRO-DEL (5'-TCTATAGCGATAGAACT-GTTTGATCTGG-GTAGC; SEQ ID NO: 23). Then, the resulting promoter was digested using HindIII and BamHI from the T-vector, and its nucleotide sequence (SEQ ID NO: 1) was confirmed by standard sequencing procedures.

(2) Cloning of Promoter pZmTE1 of Mei2-Like Gene from Corn

The 5' end sequence of ZmTE1 was amplified by PCR using the designed primers pZmTE1-F (5'- AGAAAGCT-TAGTGCCAATCACTGCGTGAGAACCGA; SEQ ID NO: 24) and pZmTE1-R (5'-AGGGGATCCTCCACTCCCTC-CCCCACCCTCCA; SEQ ID NO: 25). The PCR conditions were: 95° C. for 5 min, then 30 cycles of 95° C. for 1min, 58° C. for 1 min, 72° C. for 1 min, then extend at 72° C. for 5 min. The resulting PCR product of about 2 Kb in length was cloned into T-vector pMD19 (TaKaRa). Since there's a BamHI site in this DNA fragment, the 1.4 kb promoter was obtained by a HindIII digestion following with a partial digestion of BamHI. The nucleotide sequence of the promoter (SEQ ID NO: 2) was confirmed by DNA sequencing using standard procedures.

(3) Cloning of Promoter pGmTE1 of Mei2-Like Gene from Soybean

The 5' end sequence of GmTE1 was amplified by PCR using the designed primers pGmTE1-F (5'-AGGAAGCTT-GAAAGAACGTAGTCCCTTCTTAAAAATGGT; SEQ ID NO: 26) and pGmTE1-R (5'-AGGGGATCCTCAAATCT-CACTCACTCGCCTCTTTTCCTCA; SEQ ID NO: 27). The PCR conditions were: 95° C. for 5 min, then 30 cycles of 95° C. for 1 min, 58° C. for 1 min, 72° C. for 1 min, then extend at 72° C. for 5 min. The resulting PCR product of about 2.5Kb in size was cloned into T-vector pMD19 (TaKaRa). The 2.5 kb promoter was digested by HindIII and BamHI from the T-vector, and its nucleotide sequence (SEQ ID NO: 3) was confirmed by sequencing using standard procedures.

(4) Cloning of promoter pAtTE1 of Mei2-like gene from *Arabidopsis thaliana*

The 5' end sequence of AtTE1 was amplified by PCR using the designed primers pAtTE1-F (5' AGGAAGCT-TACTTCGTGTTTAACAAACA; SEQ ID NO: 28) and pAtTE1-R (5'- AGGGGATCCTAATACCAGAGTTGA-TAGGGGCC: SEQ ID NO: 29). The PCR conditions were: 95° C. for 5 min, then 30 cycles of 95° C. for 1 min, 58° C. for 1min, 72° C. for 1 min, then extend at 72° C. for 5 min. The resulting PCR product of about 1.7 Kb in size was cloned into T-vector pMD19 (TaKaRa). The 1.7 kb promoter was digested by HindIII and BamHI from the T-vector, and its nucleotide sequence (SEQ ID NO: 5) was confirmed by sequencing using standard procedures.

(5) Cloning of Promoter pAtML1 of Mei2-Like Gene from *Arabidopsis thaliana*

The 5' end sequence of AtML1 was amplified by PCR using the designed primers pAtML1-F (5' -AGAAAGCT-TACTTAGCCCTATGAGCTTAAC; SEQ ID NO: 30) and pAtML1-R (5'- AGAGGATCCAAACCCAAATTGCCTCT-GCC; SEQ ID NO: 31). The PCR conditions were: 95° C. for 5 min, then 30 cycles of 95° C. for 1 min, 58° C. for 1 min, 72° C. for 1 min, then extend at 72° C. for 5 min. The resulting PCR product of about 3.2Kb in size was cloned into T-vector pMD19 (TaKaRa). The 3.2 kb promoter was digested by HindIII and BamHI from the T-vector, and its nucleotide sequence (SEQ ID NO: 7) was confirmed by sequencing using standard procedures.

(6) Cloning of Promoter pBrTE1 of Mei2-Like Gene from *Brassica rupa*

The 5' end sequence of BrTE1 was amplified by PCR using the designed primers pBrTE1-F (5'- AAGCTTC-CCAAATTTAATCGAACC; SEQ ID NO: 32) and pBrTE1-R (5'- GGATCCTTTAATTATTTTCTTACGGGA; SEQ ID NO: 33). The PCR conditions were: 95° C. for 5 min, then 30 cycles of 95° C. for 1 min, 58° C. for 1 min, 72° C. for 1 min, then extend at 72° C. for 5 min. The resulting PCR product of about 2.2 Kb fragment was cloned into T-vector pMD19 (TaKaRa). The 2.2 kb promoter was digested by HindIII and BamHI from the T-vector, and its nucleotide sequence (SEQ ID NO: 8) was confirmed by sequencing using standard procedures.

(7) Cloning of Promoter pOsFCA of FCA Homologous Gene from Rice

The 5' end sequence of OsFCA was amplified by PCR using the designed primers pOsFCA-F (5'- AAGCTTT-GAGGGATGTTAGGTCTCGA; SEQ ID NO: 34) and pOs-FCA-R (5'-GGATCCGTGGGTGGAGGGGGAGGTGGG; SEQ ID NO: 35). The PCR conditions were: 95° C. for 5 min, then 30 cycles of 95° C. for 1 min, 58° C. for 1 min, 72° C. for 1 min, then extend at 72° C. for 5 min. The resulting PCR product of about 2.2Kb fragment was cloned into T-vector pMD19 (TaKaRa). Since there's a HindIII site in this DNA fragment, the 2.2 Kb promoter was obtained by a BamHI digestion following with a partial digestion of HindIII. The nucleotide sequence of the promoter (SEQ ID NO: 9) was confirmed by DNA sequencing using standard procedures.

Example 2

Artificial Synthesis of the Auxin Synthase Genes

The coding sequences and terminators of the auxin synthase genes were synthesized artificially by Shanghai Sangon Limited, China. The genes from *Agrobacterium tumefaciens* and *Peudomonas syringae* are Ps-iaaM (SEQ ID NO: 11) and Ag-iaaM (SEQ ID NO: 12). The encoded amino acid sequences of these auxin synthase genes are listed in SEQ ID NOs:14 and 15 respectively. The restriction sites of BamHI and HindIII were added to its 5' and 3' end of the gene respectively. The two designed genes (SEQ ID NO: 11 and SEQ ID NO: 12) were then synthesized artificially. Similarly, gene Os-YC from the key enzyme of auxin synthesis was also obtained by gene synthesis, and has a BamHI site in the 5' end and a KpnI and a HindIII site on the 3' end. The Os-YC's nucleotide sequence is SEQ ID NO: 13 (including the terminator).

Example 3

Construction of Vectors Harboring T-DNA with the Expression Cassettes of the Auxin Synthase Genes pCambia 1300 was used to construct *Agrobacterium*-mediated transformation vectors for plants. The promoter was digested with HindIII and BamHI, and then ligated using a 3-way ligation reaction with the auxin synthase genes predigested with BamHI and KpnI, and the pCambia 1300 predigested with HindIII and KpnI. The promoter fragments are pOsTE1, pZmTE1, pGmTE1, pAtTE1, pAtML1 and pBrTE1. The auxin synthase gene fragments are Ag-iaaM and Ps-iaaM. The resulted T-DNA constructs were separately named as:

1) pCambia1300-pOsTE1-Ag-iaaM
2) pCambia1300-pOsTE1-Ps-iaaM
3) pCambia1300-pZmTE1-Ag-iaaM
4) pCambia1300-pZmTE1-Ps-iaaM
5) pCambia1300-pGmTE1-Ag-iaaM
6) pCambia1300-pGmTE1-Ps-iaaM
7) pCambia1300-pAtTE1-Ag-iaaM
8) pCambia1300-pAtTE1-Ps-iaaM
9) pCambia1300-pAtML1-Ag-iaaM
10) pCambia1300-pAtML1-Ps-iaaM
11) pCambia1300-pBrTE1-Ag-iaaM
12) pCambia1300-pBrTE1-Ps-iaaM Example 4

Rice Transformation

Rice transformation via *Agrobacterium*-mediated method is well established in the art (Lu & Gong (1998) *Chinese Bulletin of Life Sciences* 10: 125-131 and Liu et al. (2003) *Molecular Plant Breeding* 1: 108-115). The cultivar *Oryza sativa (japonica)* "Xiushui 134" was used in transformation.

The single clones of *Agrobacterium* strain LBA4404 containing the binary vectors of pCambia1300-pOsTE1-Ag-iaaM, pCambia1300-pOsTE1-Ps-iaaM, pCambia1300-pZmTE1-Ag-iaaM and pCambia1300-pZmTE1-Ps-iaaM, respectively, were separately cultured for infecting calli. The prepared calli were immersed in the bacteria cell suspension (OD595≈0.4, containing 20 mg/L of acetosyringone) for 25 min. Then, the calli were transferred to the co-culture medium (containing 20 mg/L of acetosyringone) and incubated for 2~3 days in the dark at 28° C. After co-cultivation, the callus tissues were washed with sterile water and then transferred to selective medium with an appropriate concentration of hygromycin for two months (successively cultured one time in the middle time of this time frame). After selection, the vigorously growing transgenic calli were transferred to pre-differentiation medium for an incubation of about 20 days. Then, the pre-differentiated calli were transferred to the differentiation medium and incubated for differentiating and sprouting with a photoperiod of 14 h per day. After 2~3 weeks, the resistant regenerating plantlets were transferred to the rooting medium. The well-grown regenerated plantlets were washed of excess agar and transplanted to soil in a greenhouse. Approximately 100 independent TO rice transformants were generated for each construct. The events with high yield, big seeds, or high biomass traits, which can increase rice output, were chosen for breeding new varieties.

Example 5

Corn Transformation

Corn transformation via *Agrobacterium* is a well-established procedure in the art (Vladimir Sidorov & David Duncan, in M. Paul Scot, ed., Methods in Molecular Biology: Transgenic Maize, vol: 526; Ishida et al. (2007) *Nature Protocols* 2: 1614-1622). Briefly, *Agrobacterium* strain LBA4404 harboring T-DNA construct pCambia1300-pOsTE1-Ag-iaaM, pCambia1300-pOsTE1-Ps-iaaM, pCambia1300-pZmTE1-Ag-iaaM and pCambia1300-pZmTE1-Ps-iaaM, respectively, was prepared to infect the immature embryos of corn Hi-II of 8-10 days after fertilization (1.0-1.5 mm). The immature embryos were incubated with the *Agrobacterium* for 2-3 days at 22° C. on the co-culture medium (MS, 2 mg/L 2,4-D, 30 g/L sucrose, 8 g/L agar of sigma 7921, 40 mg/L acetosyringone), and then were moved to callus induction medium (MS, 2 mg/L 2,4-D, 30 g/L sucrose, 2.5 g/L gelrite, 5 mg/L AgNO$_3$, 200 mg/L timentin) for an incubation of 10-14 days at 28° C. in the dark. For selection of transformed cells. The calli were moved to selection medium (the same gradients with callus induction media) containing 50 mg/L hygromycin. After 2-3 weeks selection, all the tissues were transferred onto fresh selection medium for another 2-3 weeks. The surviving embryogenic tissues were moved to regeneration medium (MS, 30 g/L sucrose, 0.5 mg/L KT, 2.5 g/L gelrite, 200 mg/L timentin) and cultured for 10-14 days at 28° C. in the dark. Then they were transferred onto fresh regeneration media for another 10-14 days at 26° C. in the light. The fully developed plants were then moved to rooting medium (½ MS, 20 g/L sucrose, 2.5 g/L gelrite, 200 mg/L timentin) and cultured at 26° C. in the light until the roots grew well. The plantlets survived were moved to green house for growth to produce seeds.

Example 6

Evaluation of Transgenic Plants

Total of 55 independent transgenic corn events were obtained from transformation of pCambia1300-pZmTE1-Ps-iaaM. In these transgenic events, IAA synthase from *Pseudomonas syringae* was under the control of TE1 promoter of *Zea mays*. Four events were evaluated for their yield enhancement potential. The weight of the ears of the transgenic plants was 5%, 8%, 10%, and 11% more than the null segregants, respectively. The plant height was also about 5, 15, 24 and 28 cm taller than the null segregants.

A total of 40 independent transgenic corn events were obtained from transformation of pCambia1300-pOsTE1-Ps-iaaM. In these transgenic events, IAA synthase from *Pseudomonas syringae* was under the control of TE1 promoter of *Oryza sativa*. Events OA-3, OA-19, and OA-26 were evaluated for their yield enhancement potential. The weight of the ears of the transgenic plants was 9%, 12%, and 8% more than the null segregants, respectively. The plant height was also about 5, 11 and 14 cm taller than the null segregants.

Total of 51 independent transgenic rice events were obtained from transformation of pCambia1300-pOsTE1-Ps-iaaM. In these transgenic events, IAA synthase from *Pseudomonas syringae* was under the control of TE1 promoter of *Oryza sativa*. Among the 51 events, event OsA-29 was the only one that showed phenotype of yield enhancement. OsA-29 has significantly bigger seeds, average of 31 mg, compared to 26 mg of the non-transgenic control rice.

Example 7

Canola Transformation

The methods for canola transformation is well established (Gopalan Selvaraj and Igor Kovalchuk1, 2011, New Biotechnology 29: 144-155; Wang, 2006, *Agrobacterium* transformation Protocols Second Edition Volume 1. Humana Press). The method is as follows: seeds of winter canola or spring canola sterilized by 20% NaClO were germinated on MS medium (30 g/L sucrose and 6 g/L agar) for 8-day. The hypocotyls from the 8-d old seedlings were cut into about 0.5-1.0 cm pieces and pre-conditioned for 3 d on callus induction medium (MS, 1 mg/L 2,4-D) at 25° C. A single colony of *Agrobacterium* stain LBA4404 harboring binary vector pCambia1300-pAtTE1-Ag-iaaM, pCambia1300-pAtTE1-Ps-iaaM, pCambia1300-pAtML1-Ag-iaaM, pCambia1300-pAtML1-Ps-iaaM, pCambia1300-pBrTE1-Ag-iaaM and pCambia1300-pBrTE1-Ps-iaaM separately was cultured in YEP liquid medium with antibiotics until the concentration of cell suspension reached to OD$_{600}$=1.0. The *Agrobacterium* was then pelleted by centrifugation and resuspended in MS liquid medium (containing 10 mg/L acetosyringone) to a final concentration of OD$_{600}$=0.2. Then, the preconditioned hypocotyls were immersed in the prepared *Agrobacterium* cell suspension for 5 min, blotted on sterile filter paper and transferred onto callus induction medium (MS, 1 mg/L 2,4-D, 10 mg/L acetosyringone) for cocultivation for 3 d at 22° C. After that, they were transferred to the selection medium (MS, 3 mg/L 6-BA, 5 mg/L AgNO$_3$, 400 mg/L timentin, 50 mg/L hygromycin) and cultured for 15 days. The selected explants were transferred to differentiation medium (MS, 5 mg/L BAP, 5 mg/L AgNO$_3$, 200 mg/L timentin, 10 mg/L hygromycin) until shoot regeneration. When the shoots were 5-10 mm in length, they were cut and transferred to shoot elongation medium (MS medium containing 0.05 mg/L BAP) Shoots of about 2 cm in length were transferred to the rooting MS medium for root induction. The rooted shoots were transplanted to soil in the greenhouse.

Example 8

Wheat Transformation

There are different methods for wheat transformation described specifically in various research papers including, but not limited to Wang et al., 2002, Acta Genetica Sinica 29: 260-265; Cheng et al., 1997, Plant Physiol 115: 971-980; Supartana et al., 2006, Journal of Bioscience and Bioengineering, The Society for Biotechnology, Japan 102: 162-170. The following is a brief description of the wheat transformation method via *Agrobacterium*.

The ordinary cultivars of winter wheat (*Triticum aestivum* L.), BAU170 and BAU146, were used in transformation. Immature caryopses 12-15 days after anthesis were collected and sterilized using 0.1% HgC1 for 10 min. After washing in sterile water for 3-4 times, the immature embryos were peeled from the seeds on a benchtop and placed on calli-inducing MS medium with scutellums upside for incubation at 25° C. in the dark for calli induction which were subcultured on the same medium for 20 days.

Single colonies of *Agrobacterium* strain LBA4404 harboring pCambia1300-pOsTE1-Ag-iaaM, pCambia1300-pOsTE1-Ps-iaaM, pCambia1300-pZmTE1-Ag-iaaM, and pCambia1300-pZmTE1-Ps-iaaM, respectively, were separately cultured in 5 ml YEB liquid medium containing the selective antibiotics and shaken on an orbital shaker with 200 rpm at 28° C. overnight. 0.5 ml of above bacterial solution was added to 50 ml YEB medium containing the same antibiotics. When the bacteria grew to $OD_{600}$=0.6, the cultures were centrifuged at 5000 rpm for 5 min. The bacteria cells were collected and resuspended in MS liquid medium (MS with 3% sucrose, pH 5.4) after being washed by the medium twice. The bacteria concentration was adjusted to $OD_{600}$=0.1~1.0. Before infection, part of the peeled immature embryos or the calli derived from the embryos were soaked into high osmotic MS medium containing 0.4 mol/L mannitol for pre-incubation for 12 h or placed on the MS medium containing 200 mmol/L acetosyringone (AS) for an 3 d pre-incubation. Then, the immature embryos or the calli were infected with the *Agrobacterium* in the cell suspension for 0.5-3.5 h. After the bacteria liquid being discarded, the explants were dried using sterile filter paper and transferred to co-culture medium (containing 200 mmol/L AS) for an incubation of 3 days at 26-28° C. in dark. Then, the explants were transferred to selection medium with containing 50 mg/L hygromycin. After being further selected on the selection medium containing 350 mg/L Cef and 50 mg/L hygromycin for 4-8 weeks at 26-28° C. in the dark, the resistant calli were transferred to the differentiation medium (MS, 10 mg/L indoleacetic acid (IAA), 1.0 mg/L ZT, 3% sucrose, 0.7% agar, pH 5.8) containing 350 mg/L Cef and 3-5 mg/L hygromycin and induced for differentiation in light. The plantlets derived by differentiation were transplanted to the rooting medium for root development.

Example 9

Soybean Transformation

The genetically transformation method for soybean is well established in the art (Kan Wang, 2006, *Agrobacterium* transformation Protocols, Second Edition, Volume 1, Humana Press; Ma et al. (2008) *Scientia Agricultura Sinica* 41(3): 661-668). The detailed description of soybean transformation method is as following. The healthy, plump and mature soybeans were surface-sterilized with chlorine gas inside a bell jar under a fume hood. Seeds were kept in Petri dishes with chlorine gas produced by pouring 100 mL of 4% sodium hypochlorite into a beaker and adding 5 mL of 12N hydrochloric acid. The sterile soybeans were sowed into B5 medium and incubated at 25° C. with a photoperiod of 18 h light and 6 h dark for pre-germination. When the cotyledon turned green and the first euphylla had not grown out completely, the seed husk, the root and the prophyll were removed. The remaining cotyledon with 3-5 cm of hypocotyl was cut in the middle vertically. The resulted two pieces of explant materials with one cotyledon, half hypocotyl and half epicotyl of each were planted in the co-culture medium (1/10 B5 major and trace elements, 1/10 MS Fe salts, B5 vitamins, 3% sucrose, 1 mg/L BA, 200 μmol/L acetosyringone, pH 5.4) for an pre-incubation with the cotyledon and embryonic tip upside.

Single colonies of *Agrobacterium* strain LBA4404 containing vector pCambia1300-pGmTE1-Ag-iaaM, pCambia1300-pGmTE1-Ps-iaaM, pCambia1300-pGmFCA-Ag-iaaM and pCambia1300-pGmFCA-Ps-iaaM, respectively, were separately cultured till the cell suspension reached to a concentration of $OD_{600}$=0.8-1.0. After centrifugation for 10 min, the cells were collected and resuspended in the co-culture medium. The explants pre-incubated for 24 h were transferred to the prepared *Agrobacterium* suspension for approximately 30 minute. The infected explants were plated adaxial or wounded side down on the filter paper overlaying co-culture medium and incubated at 25° C. for 3 days. Then, the explants were washed off the excess bacteria and transferred to shoot-inducing medium (B5 major and trace elements, MS Fe salts, 3% sucrose, 1.68 mg/L BAP, 400 mg/L timentin, 50 mg/L hygromycin, 2.5 g/L gelrite, pH 5.6) for a 14-day incubation at 25° C. After another 14-day incubation in the shoot-inducing medium containing 50 mg/L hygromycin, the cotyledon and the dead tissue of the explants were cut off, and the explants were transferred to shoot-elongation medium (MS major and trace elements and Fe salts, B5 vitamins, 3% sucrose, 0.1 mg/L IAA, 0.5 mg/L GA3, 1 mg/L ZR, 200 mg/L timentin, 2.5 g/L gelrite, pH 5.6) for a 14-day incubation. Finally, the healthy shoots with at least 3 leaves were transferred to the rooting medium (½ B5, MS Fe salts, 2% sucrose, 1 mg/L IBA, pH 5.6) for root development.

The invention used many techniques in molecular biology, biochemistry and tissue culture. These techniques are available in the art. Detailed methods of the techniques can be referenced in Current Protocols in Molecular Biology (ed. by Ausubel, John Wiley and Sons Press) and Molecular Cloning: A Laboratory Manual, 3rd ED (ed. by J. Sambrook, Cold Spring Harbor Laboratory Press (2001).

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

| SEQ ID NO: | description | Note |
|---|---|---|
| 1 | Promoter of *Oryza sativa* TE1 | DNA |
| 2 | Promoter of *Zea mays* TE1 | DNA |
| 3 | Promoter of *Glycine max* TE1 | DNA |
| 4 | Promoter of *Glycine max* TE2 | DNA |
| 5 | Promoter of *Arabidopsis thaliana* TEL1 | DNA |
| 6 | Promoter of *Arabidopsis thaliana* TEL2 | DNA |
| 7 | Promoter of *Arabidopsis thaliana* AtML1 | DNA |
| 8 | Promoter of *Brassica rapa* TE1 | DNA |
| 9 | Promoter of *Oryza sativa* FCA | DNA |
| 10 | Promoter of *Glycine max* FCA | DNA |
| 11 | *Peudomonas syringae* IAAM | Artificial synthesis cDNA |
| 12 | *Agrobacterium tumefaciens* IAAM | Artificial synthesis cDNA |
| 13 | *Oryza sativa* flavin-containing monooxygenase-like (Os-YC) | Artificial synthesis cDNA (including the terminator) |
| 14 | *Peudomonas syringae* IAAM | Protein |
| 15 | *Agrobacterium tumefaciens* IAAM | protein |
| 16 | *Dickeya dadantii* IAAM | protein |
| 17 | *Pantoea agglomerans* IAAM | protein |
| 18 | *Agrobacterium vitis* IAAM | protein |
| 19 | *Arabidopsis thaliana* YUCCA family monooxygenase (YUC1) | protein |

That which is claimed:

1. A method for increasing plant yield in a plant of interest, said method comprising
transforming said plant with a DNA construct comprising a promoter that drives expression in a plant shoot meristem and inflorescence operably linked to an auxin synthase coding sequence wherein said auxin synthase coding sequence is selected from the group consisting of:
i) the sequence set forth in SEQ ID NO:11, 12, or 13;
ii) a sequence having at least 60% sequence identity to the sequence set forth in SEQ ID NO:11, 12, or 13;
iii) a nucleotide sequence that encodes the amino acid sequence set forth in any one of SEQ ID NOs:14-18; and,
iv) a nucleotide sequence that encodes an amino acid sequence having at least 40% sequence identity to any one of SEQ ID NOs:14-18,
wherein said promoter is a promoter from a plant Mei2-like gene.

2. The method of claim 1, wherein said promoter comprises a sequence selected from the sequences set forth in SEQ ID NO:1-SEQ ID NO:10.

3. The method claim 1, wherein said auxin synthase coding sequence is from a microorganism or from a plant.

4. The method of claim 1, wherein plant is selected from the group consisting of rice, corn, cotton, wheat, barley, soybean, sunflower, canola, and sorghum.

5. An expression cassette comprising a DNA construct, said construct comprising a promoter that drives expression in a plant shoot meristem and inflorescence operably linked to an auxin synthase coding sequence, wherein said auxin synthase coding sequence is selected from the group consisting of:
i) the sequence set forth in SEQ ID NO:11, 12, or 13;
ii) a sequence having at least 60% sequence identity to the sequence set forth in SEQ ID NO:11, 12, or 13;
iii) a nucleotide sequence that encodes the amino acid sequence set forth in any one of SEQ ID NOs:14-18; and,
iv) a nucleotide sequence that encodes an amino acid sequence having at least 40% sequence identity to any one of SEQ ID NOs:14-18,
wherein said promoter is a promoter from a plant Mei2-like gene.

6. The expression cassette of claim 5, wherein said promoter comprises a sequence selected from the sequences set forth in SEQ ID NO:1-SEQ ID NO:10.

7. The expression cassette of claim 5, wherein said auxin synthase coding sequence is from a microorganism or from a plant.

8. A plant transformed with the expression cassette of claim 5.

9. A transformed seed of the plant of claim 8.

10. A transformed plant that exhibits increased expression of auxin synthase in its shoot meristem and inflorescence as compared to a control plant, said plant having been transformed with a DNA construct comprising a promoter that drives expression in a plant shoot meristem and inflorescence operably linked to an auxin synthase coding sequence, wherein said auxin synthase coding sequence is selected from the group consisting of:
   i) the sequence set forth in SEQ ID NO:11, 12, or 13;
   ii) a sequence having at least 60% sequence identity to the sequence set forth in SEQ ID NO:11, 12, or 13;
   iii) a nucleotide sequence that encodes the amino acid sequence set forth in any one of SEQ ID NOs:14-18; and,
   iv) a nucleotide sequence that encodes an amino acid sequence having at least 40% sequence identity to any one of SEQ ID NOs:14-18,
wherein said promoter is a promoter from a plant Mei2-like gene.

11. The transformed plant of claim 10, wherein said promoter comprises a sequence selected from the sequences set forth in SEQ ID NO:1-SEQ ID NO:10.

12. The transformed plant of claim 10, wherein said auxin synthase coding sequence is from a microorganism or from a plant.

13. Transformed seed from the plant of claim 10.

14. The transgenic plant of claim 10, wherein said plant is selected from the group consisting of rice, corn, cotton, wheat, barley, soybean, sunflower, canola, and sorghum.

15. An expression cassette comprising a DNA construct, said construct comprising a promoter that drives expression in a plant shoot meristem and inflorescence operably linked to an auxin synthase coding sequence, wherein said auxin synthase coding sequence is selected from the group consisting of:
   i) a nucleotide sequence that encodes the amino acid sequence set forth in SEQ ID NO: 19; and,
   ii) a nucleotide sequence that encodes an amino acid sequence having at least 40% sequence identity to SEQ ID NO: 19,
wherein said promoter comprises a nucleic acid sequence selected from the group of nucleic acid sequences set forth in SEQ ID NO:1- SEQ ID NO:10.

* * * * *